United States Patent [19]
Walewski et al.

[11] Patent Number: 6,060,271
[45] Date of Patent: May 9, 2000

[54] CDNA FRAGMENTS CORRESPONDING TO VOLTAGE GATED SODIUM CHANNEL GENES EXPRESSED IN PERIPHERAL NERVE

[75] Inventors: Jose L. Walewski, New York; Esperanza Recio-Pinto, Bayside, both of N.Y.

[73] Assignee: Cornell Research Foundation, Inc., Ithaca, N.Y.

[21] Appl. No.: 08/605,284

[22] Filed: Feb. 9, 1996

[51] Int. Cl.$^7$ .............................. C12N 15/12; C07K 14/47
[52] U.S. Cl. .................. 435/69.1; 536/23.5; 435/325; 435/252.3; 435/320.1; 530/350
[58] Field of Search ................................. 536/23.5, 24.31, 536/24.5; 435/69.1, 325, 320.1, 252.3; 530/350

[56] References Cited

U.S. PATENT DOCUMENTS

| | | |
|---|---|---|
| 5,256,540 | 10/1993 | Lennon et al. . |
| 5,264,371 | 11/1993 | Miljanich et al. . |
| 5,288,723 | 2/1994 | Strichartz et al. . |
| 5,356,775 | 10/1994 | Hebert et al. . |
| 5,364,842 | 11/1994 | Justice et al. . |
| 5,380,836 | 1/1995 | Rogart . |

OTHER PUBLICATIONS

Noda, et al. Nature vol. 320: pp 188–192, 1986.
Suzuki, et al. FEBS Letters. vol. 228(1): pp. 195–200, 1988.
Kayano, et al. FEBS Letters. vol. 228(1) pp. 187–194, 1988.
Schaller, et al. J. Neuroscience. vol. 15(5): pp 3231–3242, 1995.
Mintz, B. in Theories and Models in Cellular Transformation, Santi, et al. (eds), pp. 45–54, Academic Press, New York, NY, 1985.
Sambrook, et al in Molecular Cloning: A Laboratory Manual, 2nd ed., p. 16.3, Cold Spring Harbor Laboratory Press, Cold Spring Harbor, NY, 1989.

Fan, Z., et al., "A Putative Novel NA Channel cDNA Isolated from Mouse NB2a Neuroblastoma Cells," *Biophysical Journal Program and Abstracts*, Thirty–ninth Annual Meeting, San Franciso, California (Feb. 12–16, 1995) (Abstract).

Caldwell, J.H., et al., "A Novel Abundant Sodium Channel Expressed in Neurons and Glia," *Biophysical Journal Program and Abstracts*, Thirty–ninth Annual Meeting, San Franciso, California (Feb. 12–16, 1995) (Abstract).

Belcher, S.M., et al., "Cloning of a Novel Sodium Channel Alpha–Subunit From Schwann Cells," *Biophysical Journal Program and Abstracts*, Thirty–ninth Annual Meeting, San Franciso, California (Feb. 12–16, 1995) (Abstract).

Toledo–Aral, J.J., et al., "A One–Minute Pulse of NGF Induces Long–Term Membrane Excitability in PC12 Cells Through the Expression of Peripheral Nerve Type Sodium Channel Gene," *Biophysical Journal Program and Abstracts*, Thirty–ninth Annual Meeting, San Franciso, California (Feb. 12–16, 1995) (Abstract).

Sato, C., et al., "Distribution of Squid Putative Sodium Channel SQSCI mRNA in the Tissues of Squid," *Biophysical Journal Program and Abstracts*, Thirty–ninth Annual Meeting, San Franciso, California (Feb. 12–16, 1995) (Abstract).

*Primary Examiner*—David L. Fitzgerald
*Attorney, Agent, or Firm*—Nixon Peabody LLP

[57] ABSTRACT

The present invention is directed to isolated nucleic acid molecules encoding a voltage gated sodium channel of a peripheral nerve cell, as well as to the isolated voltage gated sodium channels of a peripheral nerve cell encoded thereby. Methods for increasing or decreasing the expression of functional voltage gated sodium channels in host cells are also provided, as well as methods using the sodium channels. Also provided is a method for isolating other voltage gated sodium channels.

27 Claims, 18 Drawing Sheets

Alignment Report of SY5Y MegAlign PATENT 2/7/96, using Clustal method with PAM250 residue weight table.
Wednesday, February 7, 1996 5:49 PM Page 5

| | | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | F | R | V | I | R | L | A | R | I | G | R | I | L | R | L | I | K | G | A | K | G | I | R | T | L | L | F | A | L | M | M | S | L | P | A | L | F | N | I | G | | + Majority |
| | | | | | | | | | | 170 | | | | | | | | | 180 | | | | | | | | | | 190 | | | | | | | | | | 200 | | | Majority |
| 156 | F | R | V | I | R | L | A | R | I | G | R | I | L | R | L | I | K | G | A | K | G | I | R | T | L | L | F | A | L | M | M | S | L | P | A | L | F | N | I | G | | SEQ ID NO-4 |
| 156 | F | R | V | I | R | L | A | R | I | G | R | I | L | R | L | I | K | G | P | K | G | I | R | T | L | L | F | A | L | M | M | S | L | P | A | L | F | N | I | G | | SEQ ID NO-5 |
| 156 | F | R | V | I | R | L | A | R | I | G | R | I | L | R | L | I | K | G | E | R | G | I | R | T | L | L | F | A | L | M | M | S | L | P | A | L | F | N | I | G | | SEQ ID NO-6 |
| 156 | F | R | V | I | R | L | A | R | I | G | R | I | L | R | L | I | K | G | A | K | G | I | R | T | L | L | F | A | L | M | M | S | L | P | A | L | F | N | I | G | | Hu Brain |
| 156 | F | R | V | I | R | L | A | R | I | G | R | V | L | R | L | I | R | G | A | K | G | I | R | T | L | L | F | A | L | M | M | S | L | P | A | L | F | N | I | G | | Hu Skm |
| 156 | F | R | V | I | R | L | A | R | I | G | R | I | L | R | L | I | R | A | A | K | G | I | R | T | L | L | F | A | L | M | M | S | L | P | A | L | F | N | I | G | | Hu TTX-ins |
| 158 | F | R | V | I | R | L | A | R | I | G | R | I | L | R | L | I | R | A | A | K | G | I | R | T | L | L | F | A | L | M | M | S | L | P | A | L | F | N | I | G | | RatSen TTX-ins |
| 156 | F | R | V | I | R | L | A | R | I | G | R | I | L | R | L | I | K | G | A | K | G | I | R | T | L | L | F | A | L | M | M | S | L | P | A | L | F | N | I | G | | Rat Bra I |
| 156 | F | R | V | I | R | L | A | R | I | G | R | I | L | R | L | I | K | G | A | K | G | I | R | T | L | L | F | A | L | M | M | S | L | P | A | L | F | N | I | G | | Rat Bra II |
| 156 | F | R | V | I | R | L | A | R | I | G | R | I | L | R | L | I | R | A | A | K | G | I | R | T | L | L | F | A | L | M | M | S | L | P | A | L | F | N | I | G | | Rat Bra III |
| 156 | F | R | V | I | R | L | A | R | I | A | R | V | L | R | L | I | R | A | V | K | G | I | R | T | L | L | F | A | L | M | M | S | L | P | A | L | F | N | I | G | | Eel |
| 157 | L | R | V | V | R | V | A | K | V | G | R | V | L | R | L | V | K | V | K | S | A | K | G | I | R | T | L | L | F | A | L | A | M | S | L | P | A | L | F | N | I | C | Drosph |
| 157 | L | R | V | V | R | V | F | R | V | G | R | V | L | R | L | I | K | W | A | K | G | M | R | K | L | L | F | S | L | A | V | S | L | P | A | L | F | N | I | G | | Sqd Stell |
| 159 | L | R | V | A | R | M | F | R | I | G | R | L | I | R | L | I | K | G | A | K | G | I | R | T | L | L | F | A | L | V | I | S | L | P | A | L | F | N | I | G | | Sqd Optic |
| 160 | L | R | V | I | R | V | F | R | L | G | R | L | L | R | F | F | D | G | A | K | G | I | R | Q | L | L | F | Q | L | L | F | T | I | V | K | S | A | P | A | L | L | N I G | Cyanea |

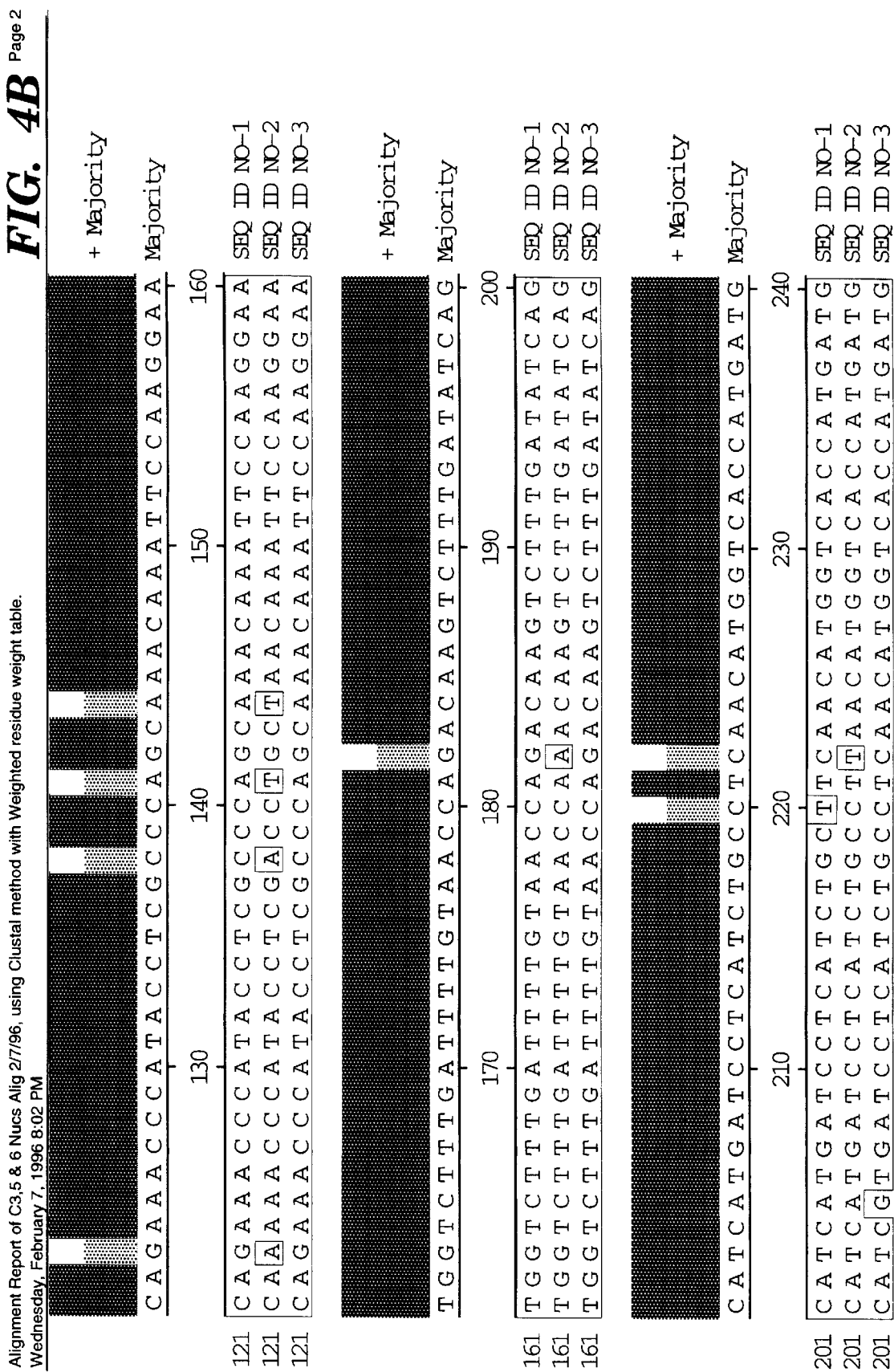
FIG. 4B Page 2

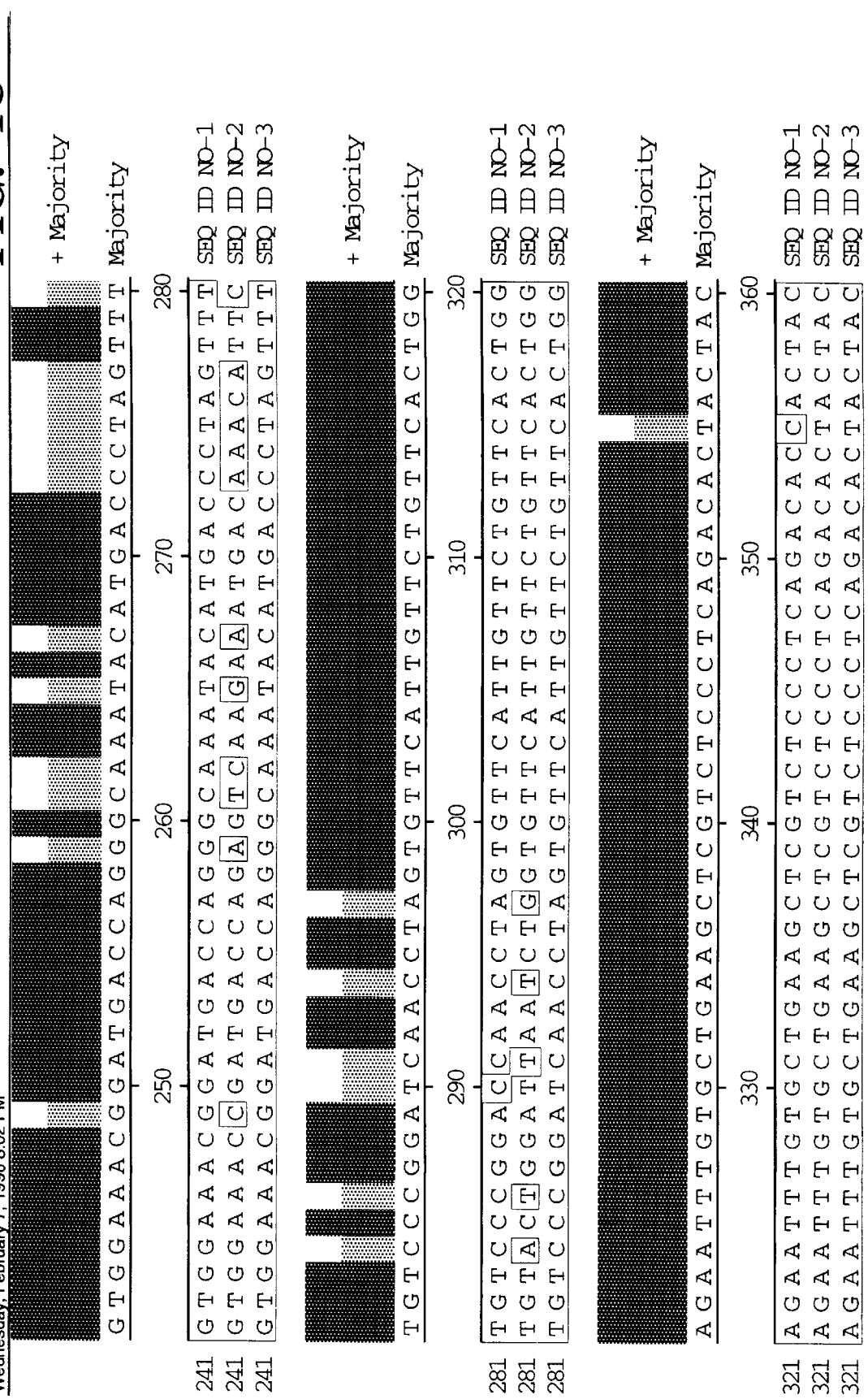
FIG. 4C Page 3

FIG. 4D Page 4

Alignment Report of C3,5 & 6 Nucs Alig 2/7/96, using Clustal method with Weighted residue weight table.
Wednesday, February 7, 1996 8:02 PM

```
                                                                              + Majority
     TTCACTATAGGCTGGAACATCTTTGACTTTGTGGTGGTGA                                 Majority
                   370       380       390       400
361  TTCACTATAGGCTGGAACATCTTTGACTTTGTGGTGGTGA                                 SEQ ID NO-1
361  TTCACTATAGGCTGGAACATCTTTGACTTTGTGGGTGGTGA                                SEQ ID NO-2
361  TTCACTATAGGCTGGAACATCTTTGACTTTGTGGTGGTGA                                 SEQ ID NO-3

+ Majority
     TTCTCTCCATTGTAGGTATGTTTCTGGCTGAGATGATAGA                                 Majority
                   410       420       430       440
401  TTCTCTCCATTGTAGGTATGTTTCTGGCTGAGATGATAGA                                 SEQ ID NO-1
401  TTCTCTCCATTGTAGGTATGTTTCTGGCTGAGATGATAGA                                 SEQ ID NO-2
401  TTCTCTCCATTGTAGGTATGTTTCTGGCTGAGATGATAGA                                 SEQ ID NO-3

+ Majority
     AAAGTATTTTGTCCCCTACCCTTGTCCGAGTGATCCGT                                   Majority
                   450       460       470       480
441  AAAGTATTTTGTCCCCTACCCTTGTCCGAGTGATCCGT                                   SEQ ID NO-1
441  AAAGTATTTTTGTCCCCTACCCTTGTCCGAGTGATCCCGT                                 SEQ ID NO-2
441  AAAGTATTTTGTCCCCTACCCTTGTCCGAGTGATCCGT                                   SEQ ID NO-3
```

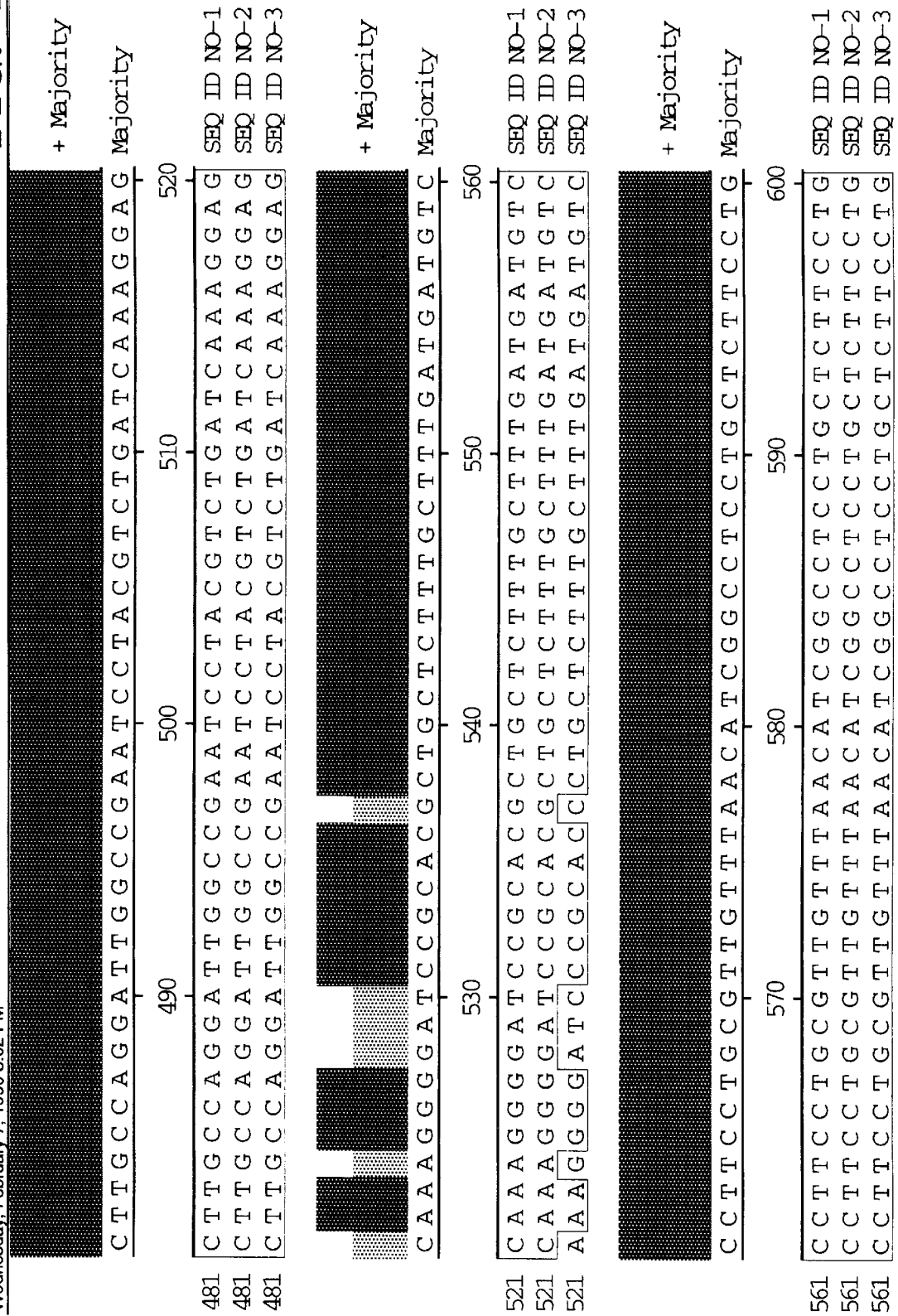

FIG. 4F

Alignment Report of C3,5 & 6 Nucs Alig 2/7/96, using Clustal method with Weighted residue weight table.
Wednesday, February 7, 1996 8:02 PM

```
            610        620        630        640
     GTCATGTTTATCTATGCCATCTTTGGGATGTCCAACTTTG         + Majority
                                                      Majority
601  GTCATGTTTATCTATGCCATCTTTGGGATGTCCAACTTTG         SEQ ID NO-1
601  GTCATGTTTATCTATGCCATCTTTGGGATGTCCAACTTTG         SEQ ID NO-2
601  GTCATGTTTATCTATGCCATCTTTGGGATGTCCAACTTTG         SEQ ID NO-3

650        660        670        680
     CCTATGTTAAAAAGGAAGCTGGAATTGATGACATGTTCAA         + Majority
                                                      Majority
641  CCTATGTAAAAAAGGAGGCTGGAATTGATGACATGTTCAA         SEQ ID NO-1
641  CCTATGTTAAAAAAGGAAGCTGGAATTGATGACATGTTCAA        SEQ ID NO-2
641  CCTATGTTAAAAAAGGAAGCTGGAATTGATGACATGTTCAA        SEQ ID NO-3

690        700        710        720
     CTTTGAGACCTTTGGCAACAGCATGATCTGCTTGTTCCAA         + Majority
                                                      Majority
681  CTTTGAGACCTTTGGCAACGGCATGATCTGCTTGTTCCAA         SEQ ID NO-1
681  CTTTGAGTCCTTTGGCAACAGCATGATCTGCTTGTTCCAA         SEQ ID NO-2
681  CTTTGAGACCTTTGGCAACAGCATGATCTGCTTGTTCCAA         SEQ ID NO-3
```

FIG. 4G Page 7

Alignment Report of C3,5 & 6 Nucs Alig 2/7/96, using Clustal method with Weighted residue weight table.
Wednesday, February 7, 1996 8:02 PM

```
          730        740        750        760
     ATTACAACCTCTGCTGGCTGGGATGGATTGCTAGCACCTA        + Majority
                                                   Majority
721  ATTACAACCTCTGCTGGCTGGGATGGATTGCTAGCACCTA       SEQ ID NO-1
721  ATTACAACCTCTGCTGGCTGGGATGGATTGCTAGCACCTA       SEQ ID NO-2
721  ATTACAACCTCTGCTGGCTGGGATGGATTGCTAGCACCTA       SEQ ID NO-3

770        780        790        800
     TTCTTAATAGTGCACCACCCGACTGTGACCCTGACACAAT        + Majority
                                                   Majority
761  TTCTTAATAGTGCACCACCCGACTGTGACCCTGACACAAT       SEQ ID NO-1
761  TTCTTAATAGTGCACCACCCGACTGTGACCCTGACACAAT       SEQ ID NO-2
761  TTCTTAATAGTGCACCACCCGACTGTGACCCTGACACAAT       SEQ ID NO-3

810        820        830        840
     TCACCCTGGCAGCTCAGTTAAGGGAGACTGTGGGAACCCA        + Majority
                                                   Majority
801  TCACCCTGGCAGCTCAGTTAAGGGAGACTGTGGGAACCCA       SEQ ID NO-1
801  TCACCCTGGCAGCTCAGTTAAGGGAGACTGTGGGAACCCA       SEQ ID NO-2
801  TCACCCTGGCAGCTCAGTTAAGGGAGACTGTGGGAACCCA       SEQ ID NO-3
```

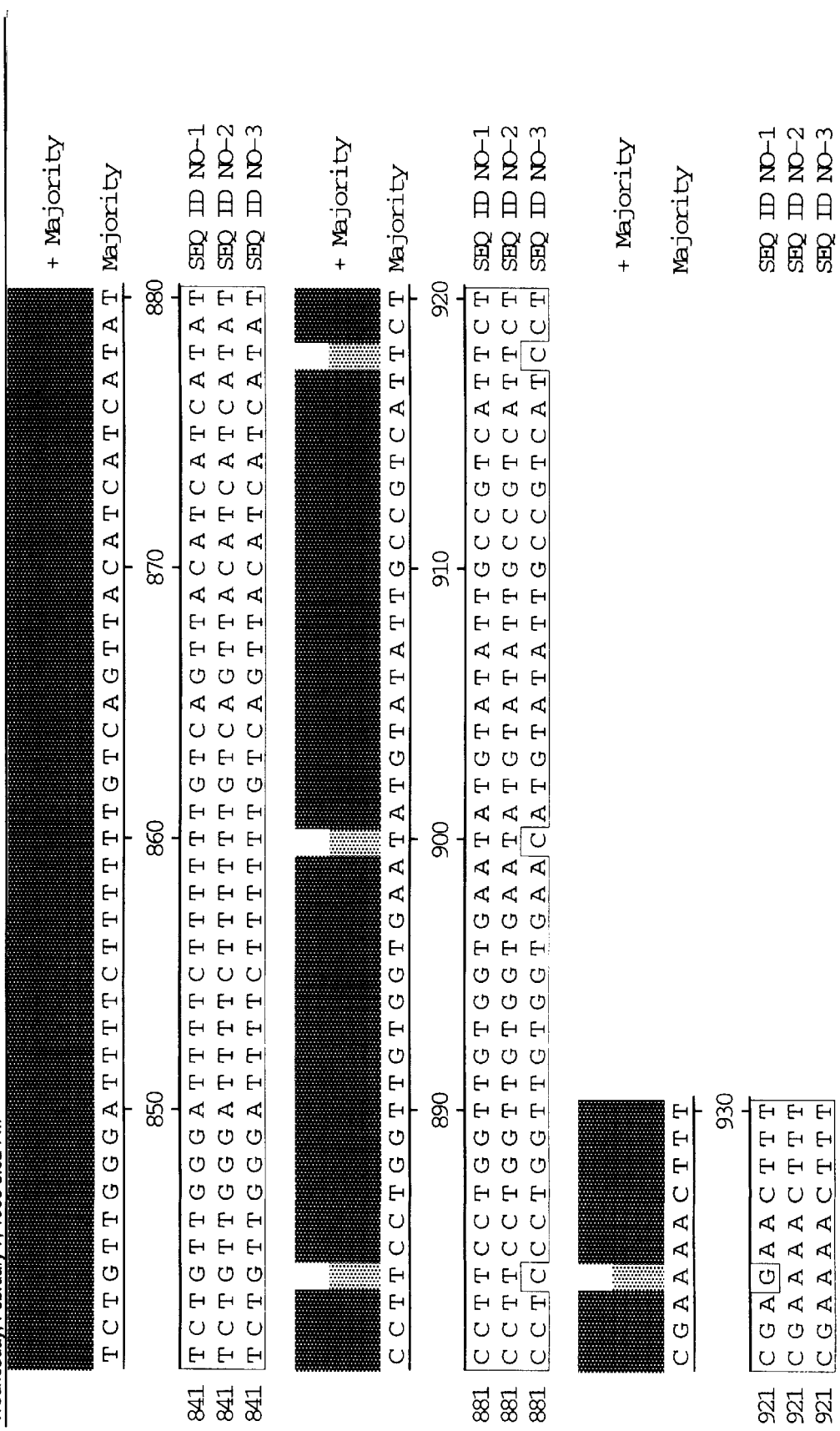

CDNA FRAGMENTS CORRESPONDING TO VOLTAGE GATED SODIUM CHANNEL GENES EXPRESSED IN PERIPHERAL NERVE

FIELD OF THE INVENTION

The present invention relates generally to sodium channel proteins, and more particularly to voltage gated sodium channels of peripheral nerve.

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

Cell membranes must allow passage of various polar molecules, including ions, sugars, amino acids, and nucleotides. Special membrane proteins are responsible for transferring such molecules across cell membranes. These proteins, referred to as membrane transport proteins, occur in many forms and in all types of biological membranes. Each protein is specific in that it transports a particular class of molecules (such as ions, sugars, or amino acids) and often only certain molecular species of the class. Most membrane transport proteins that have been studied in detail have been found to be transmembrane proteins. These proteins enable the specific molecules to cross the membrane without coming into direct contact with the hydrophobic interior of the lipid bilayer of the plasma membrane.

There are two major classes of membrane transport proteins: carrier proteins and channel proteins. Carrier proteins bind the specific molecule to be transported and undergo a series of conformational changes in order to transfer the bound molecule across the membrane. Channel proteins, on the other hand, form hydrophilic pores that extend across the lipid bilayer; when these pores are open, they allow specific molecules (usually inorganic ions of appropriate size and charge) to pass through them and thereby cross the membrane. Transport through channel proteins occurs at a much faster rate than transport mediated by carrier proteins.

Channel proteins which are concerned specifically with inorganic ion transport are referred to as ion channels, and include ion channels for sodium, potassium, calcium, and chloride ions. Ion channels which open in response to a change in the voltage across the membrane are referred to as voltage gated ion channels (or voltage-dependent ion channels).

Voltage-dependent ion channels are a class of channel proteins that play a major role in cellular electrical excitability. In the majority of excitable tissues, the early depolarization phase of action potentials is mediated by a sodium current via voltage-dependent sodium channels (also known as voltage-gated sodium channels or VGSCs).

The sodium channel is one of the most thoroughly characterized of the voltage gated channels (see FIG. 1 for a model of a voltage sensitive sodium channel). Six distinct neurotoxin or drug receptor sites have been characterized on the sodium channel, associated with channel pore or gating structures (Catterall 1986; Catterall 1988). The mechanisms by which drugs and neurotoxin agonists and antagonists act at the sodium channel and the development of general rules for how drugs interact with other ion channels having extensive homologies to sodium channels can be more readily studied once the actual structure of various sodium channels is more clearly understood.

The primary structures of many sodium channels from a variety of tissues (brain, skeletal muscle and cardiac muscle) and organisms (jellyfish, squid, eel, rat, human) have been identified, and their amino acid sequences show individual regions which are highly conserved over evolution, indicating that voltage-dependent sodium channels belong to a large superfamily of evolutionarily related proteins (Alberts et al. 1994). All published polypeptide complexes of VGSCs have in common a large, about 260 kDa glycoprotein (the pore forming subunit) which is called the alpha subunit (Agnew et al. 1978; Agnew et al. 1980; Catterall 1986; Catterall 1992). Additional lower molecular weight polypeptides, the beta-subunits, have been found to be associated with sodium channels from mammalian muscle (Kraner et al. 1985; Tanaka et al. 1983) and brain (Hartshorne and Catterall 1984). The large, pore-forming alpha subunit is sufficient for all known functions of VGSCs (Catterall 1992; Anderson and Koepe 1992), while the beta subunits modulate some of the functions of the alpha subunit (Catterall 1992; Anderson and Koepe 1992).

Cloning studies of cDNAs encoding the sodium channel large α-subunit from eel electroplax (Noda et al. 1984), rat brain (Noda et al. 1986b), and Drosophila (Salkoff et al. 1987a; Salkoff et al. 1987b) have demonstrated that: 1) the sequence of the α-subunit consists of four repeated, highly homologous hydrophobic domains (each of which contains six transmembrane segments of S1–S6) separated by hydrophilic, nonrepeated intervening sequences (see FIG. 2); 2) considerable homology exists among the sequences from different species, with the greatest conservation existing among the four internally homologous domains; 3) the S4 segment of each homologous domain is positively charged, with four to eight lysine or arginine residues at every third position, which may be involved in channel gating (Greenblatt et al. 1985; Guy et al. 1986; Noda et al. 1984); 4) in rat brain (Noda et al. 1986a; Kayano et al. 1988), three homologous genes encode four mRNA sequences (designated as types I, II, IIA, and III) which in turn encode four distinct sodium channel isoforms in the same tissue; and 5) expression of mRNA injected into oocytes, coding for the α-subunit alone of the rat brain I, II, or III sodium channels, was sufficient to produce a functional voltage-activated sodium channel (Noda et al. 1986a; Suzuki et al. 1988; Agnew 1986; Goldin et al. 1986) exhibiting many of the key properties of the native channel, including appropriate kinetics, voltage-sensitivity, ion selectivity, and sensitivity to the neurotoxin TTX. Different groups have found β-subunits important to varying extents to sodium channel function, making their role somewhat controversial (Catterall 1986; Agnew 1986; Goldin et al. 1986; Messner et al. 1986; Auld et al. 1988; Stuhmer et al. 1987).

The detection of three separate cDNA clones has led to the identification of three structurally distinct sodium channel isoforms in rat brain (Noda et al. 1986a). Two further distinct isoforms have been detected in rat skeletal muscle (Barchi 1988). Another sodium channel isoform was found in rat heart (Rogart 1995).

There continues to exist a need in the art for specific information concerning the primary structural conformation of other sodium channel proteins. Availability of such DNA sequences would make possible the application of recombinant methods to the large scale production of the proteins in prokaryotic and/or eukaryotic host cells, as well as DNA-DNA, DNA-RNA, and RNA-RNA hybridization procedures for the detection, quantification and/or isolation of nucleic acids associated with these proteins. Possession of peripheral nerve sodium channels and related sodium channel proteins and/or knowledge of the amino acid sequences of the same would make possible, in turn, the development of monoclonal and polyclonal antibodies thereto (including antibodies to protein fragments or synthetic peptides modeled thereon) for use in immunological methods for the detection and quantification of the proteins in fluid and tissue samples, as well as for tissue specific delivery of substances such as labels and therapeutic agents to cells expressing the proteins; as well as allowing for the development of new drugs.

SUMMARY OF INVENTION

To this end, it is an object of the subject invention to provide an isolated nucleic acid molecule encoding a voltage gated sodium channel of a peripheral nerve cell, preferably a human peripheral nerve cell, as well as to provide an antisense nucleic acid molecule complementary to mRNA encoding a voltage gated sodium channel of a peripheral nerve cell.

The isolated nucleic acid molecules of the invention can be inserted into suitable expression vectors and/or host cells. Expression of the nucleic acid molecules encoding the sodium channels results in production of functional sodium channels in a host cell. Expression of the antisense nucleic acid molecules or fragments thereof in a host cell results in decreased expression of the functional sodium channels.

The invention further provides the information for the production of antisense molecules, which are sequences complementary to mRNA encoding VGSCs of peripheral nerve cells. The antisense molecules may be designed to include a ribozyme moiety (an RNA sequence which cleaves RNA). The antisense can be introduced into a cell to also achieve decreased expression of sodium channels in the cell.

The invention further provides a method of screening a chemical agent for the ability of the chemical agent to modify sodium channel function, and a method of obtaining DNA encoding a voltage gated sodium channel of a peripheral nerve cell.

Further provided is an isolated nucleic acid molecule encoding a voltage gated sodium channel of a peripheral nerve cell, wherein the nucleic acid molecule encodes a first amino acid sequence which includes a second amino acid sequence having at least 95% amino acid identity to a third amino acid sequence. The third amino acid sequence is, in three preferred embodiments, SEQ ID NO:4, SEQ ID NO:5, or SEQ ID NO:6.

The invention also provides an isolated voltage gated sodium channel of a peripheral nerve cell, and antibodies or antibody fragments specific for the sodium channel. The antibodies or antibody fragments can be used to detect the presence of the sodium channel in samples.

Further provided is an isolated voltage gated sodium channel of a peripheral nerve cell, wherein the voltage gated sodium channel is encoded by a first amino acid sequence which includes a second amino acid sequence having at least 95% amino acid identity to a third amino acid sequence. In three preferred embodiments, the third amino acid sequence is SEQ ID NO:4, SEQ ID NO:5, or SEQ ID NO:6.

BRIEF DESCRIPTION OF THE DRAWINGS

These and other features and advantages of this invention will be evident from the following detailed description of preferred embodiments when read in conjunction with the accompanying drawings in which:

Figure 3G:
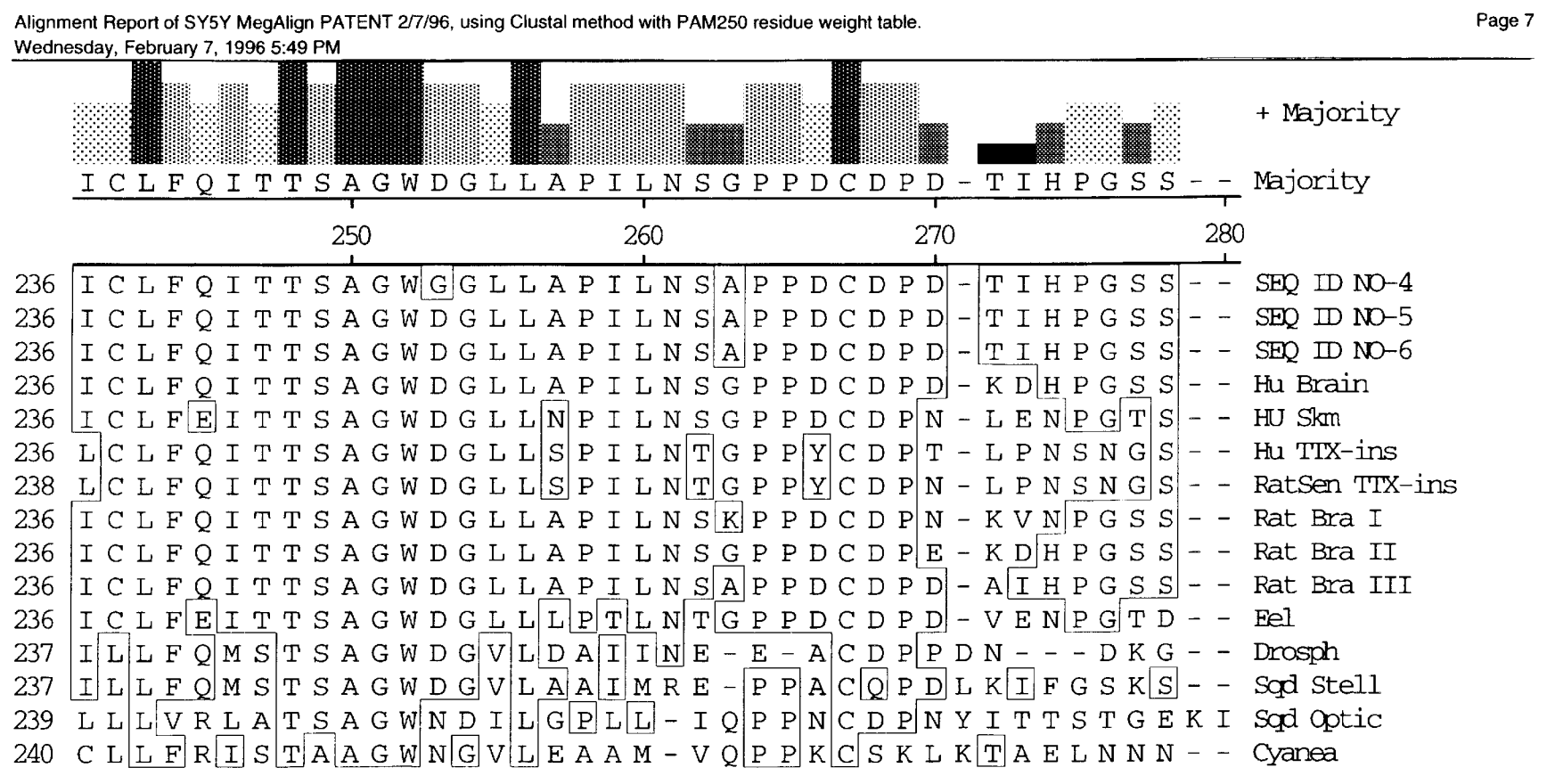

FIGS. 3A–3H show the alignment of the amino acid sequences of the sodium channels from human peripheral nerve according to the subject invention to various other sodium channels; and FIGS. 4A–4H show the alignment of the amino acid and nucleotide sequences of the three sodium channels from human peripheral nerve according to the subject invention.

DETAILED DESCRIPTION

Figure 1:
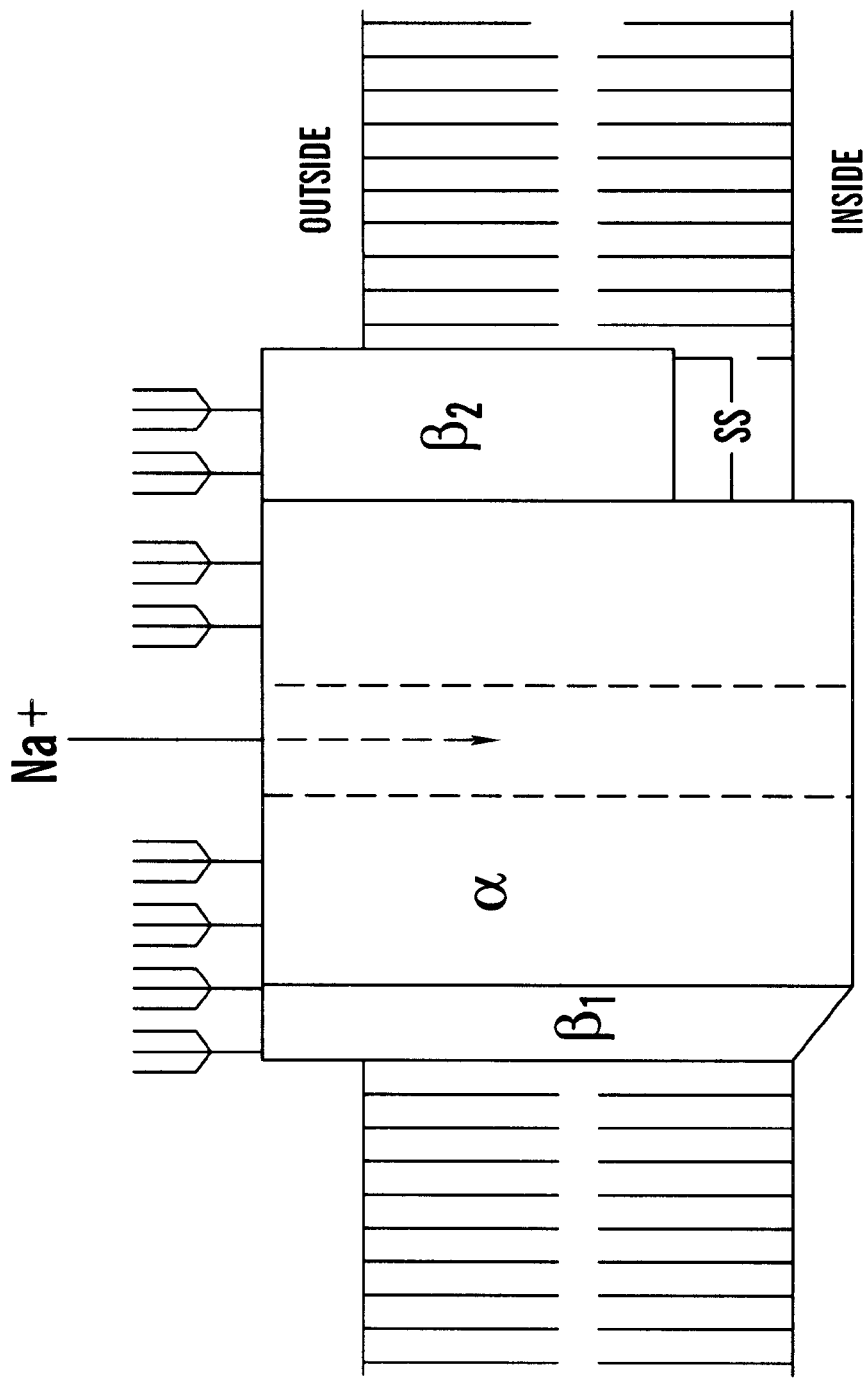
FIG. 1 is a model of a voltage sensitive sodium channel from mammalian brain in the plasma membrane. The alpha and beta$_1$ subunits interact noncovalently; the alpha and beta$_2$ subunits are linked by disulfide bonds. The branched structures at the outer surface of the channel represent oligosaccharides (Catterall 1988a)
Figure 2:
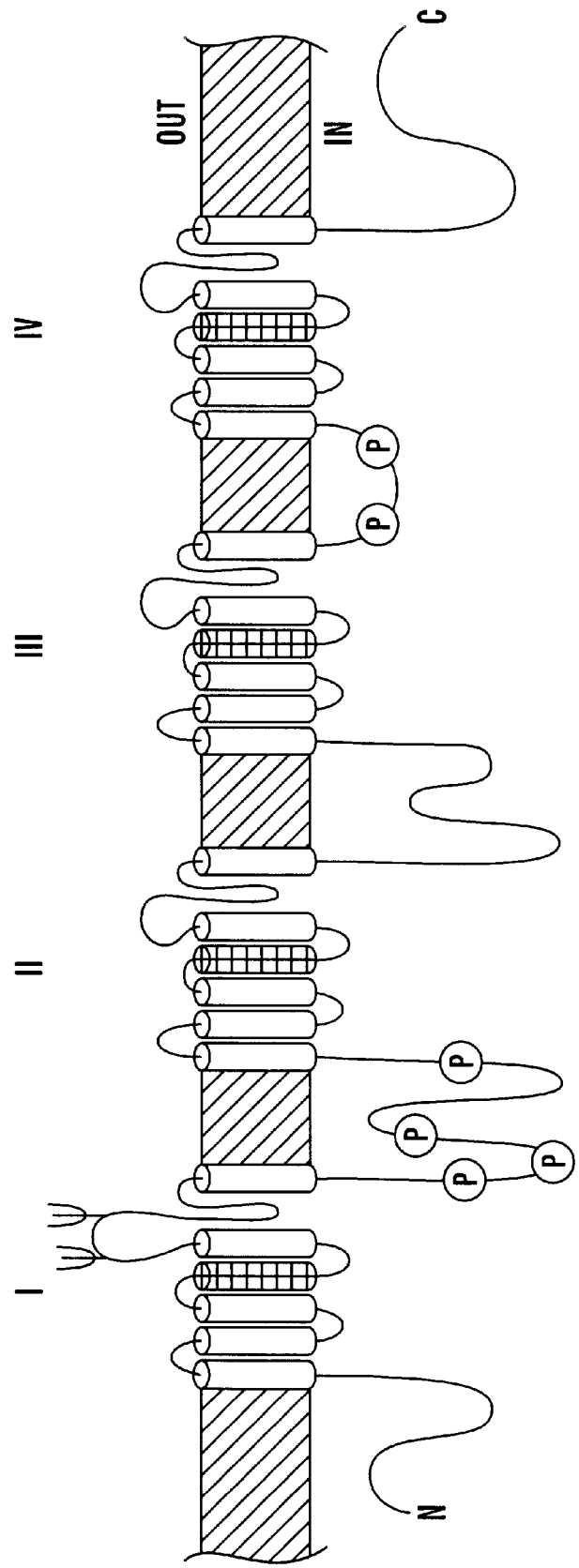
FIG. 2 is a proposed transmembrane arrangement of the alpha subunit of a sodium channel. Four homologous domains (I–IV) each consist of six stretches of hydrophobic amino acid residues that are thought to cross the plasma membrane. The S4 segment contains positively charged residues (Anderson and Koepe 1992)
Figure 3A:
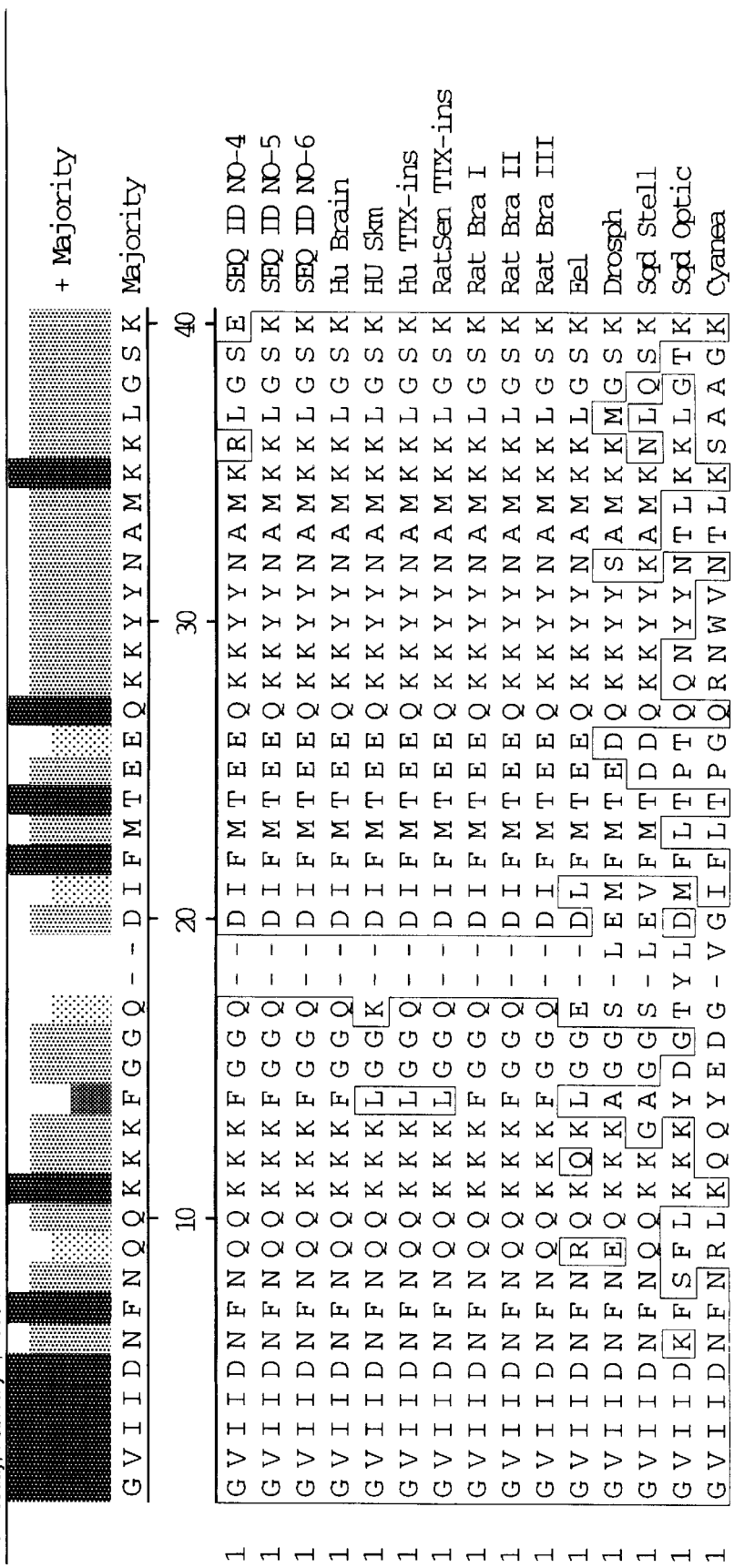
Figure 3B:
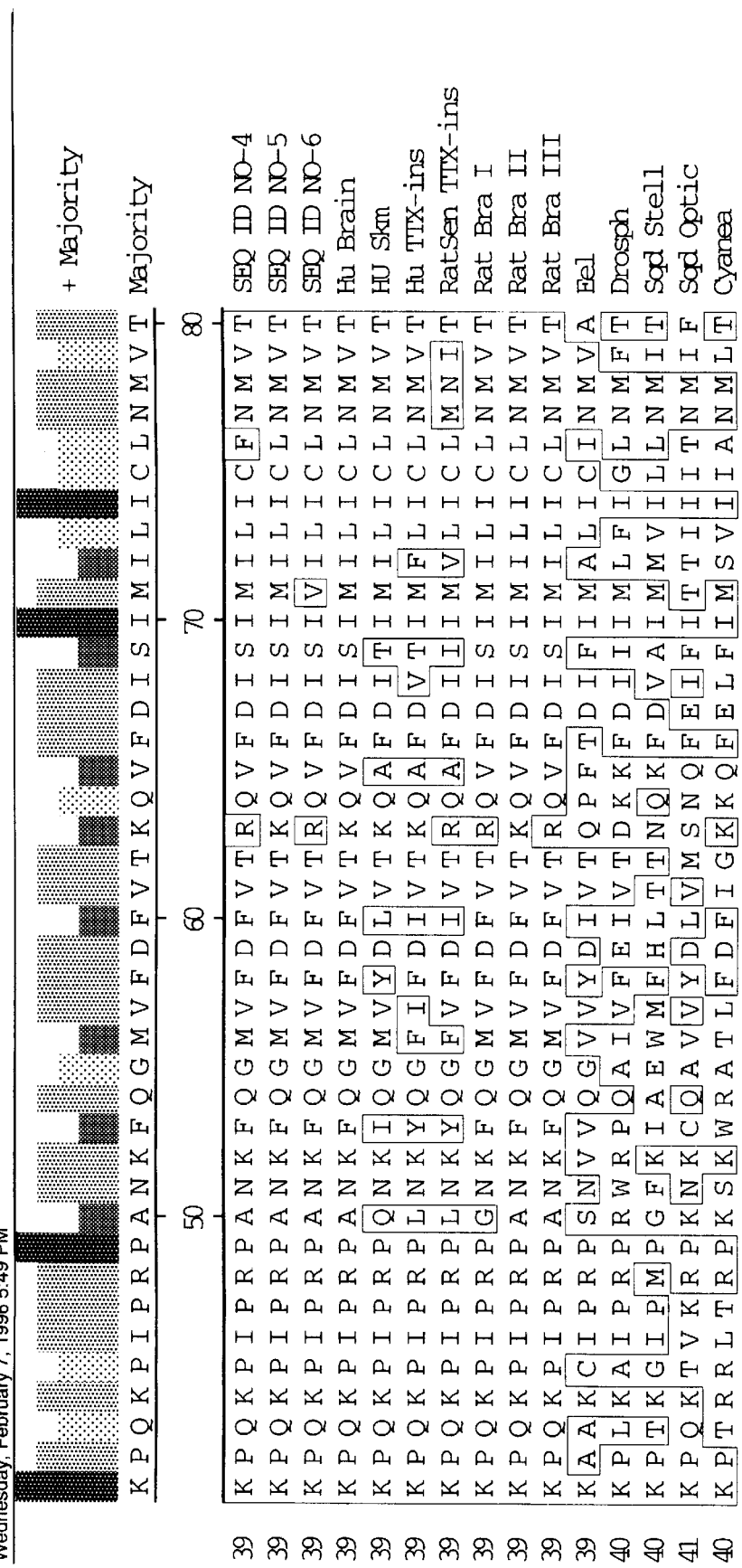
Figure 3C:
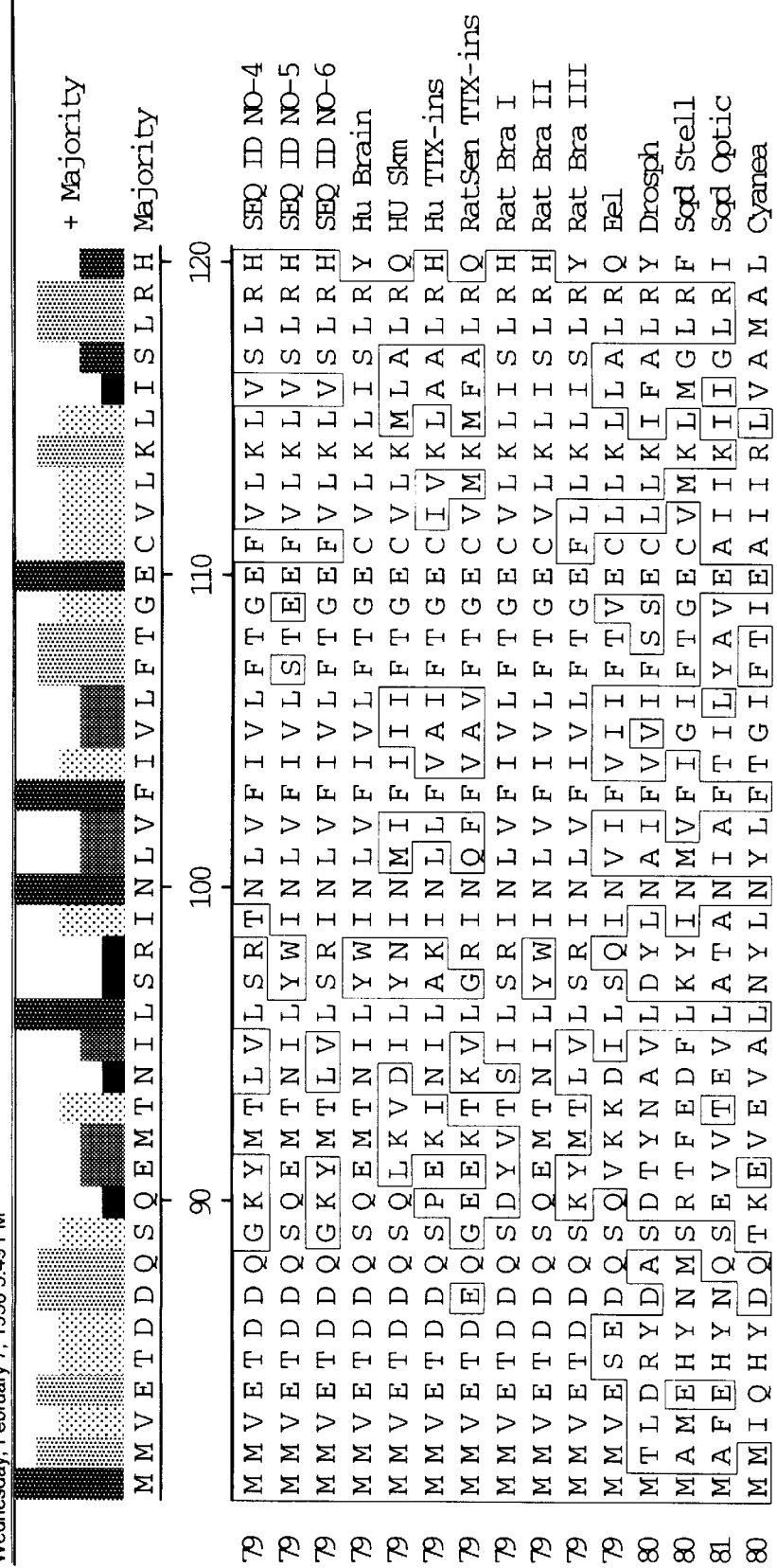
Figure 3D:
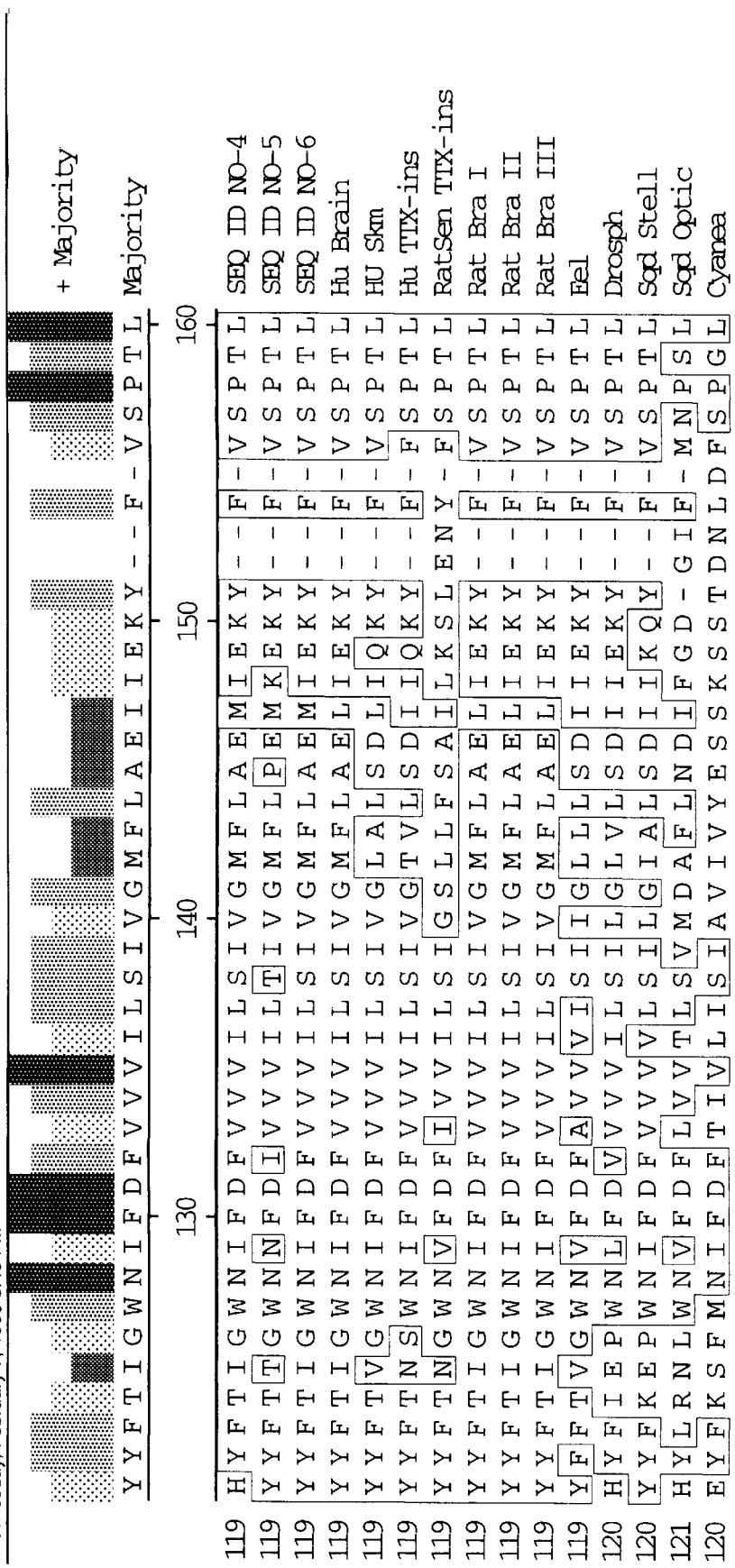
Figure 3F:
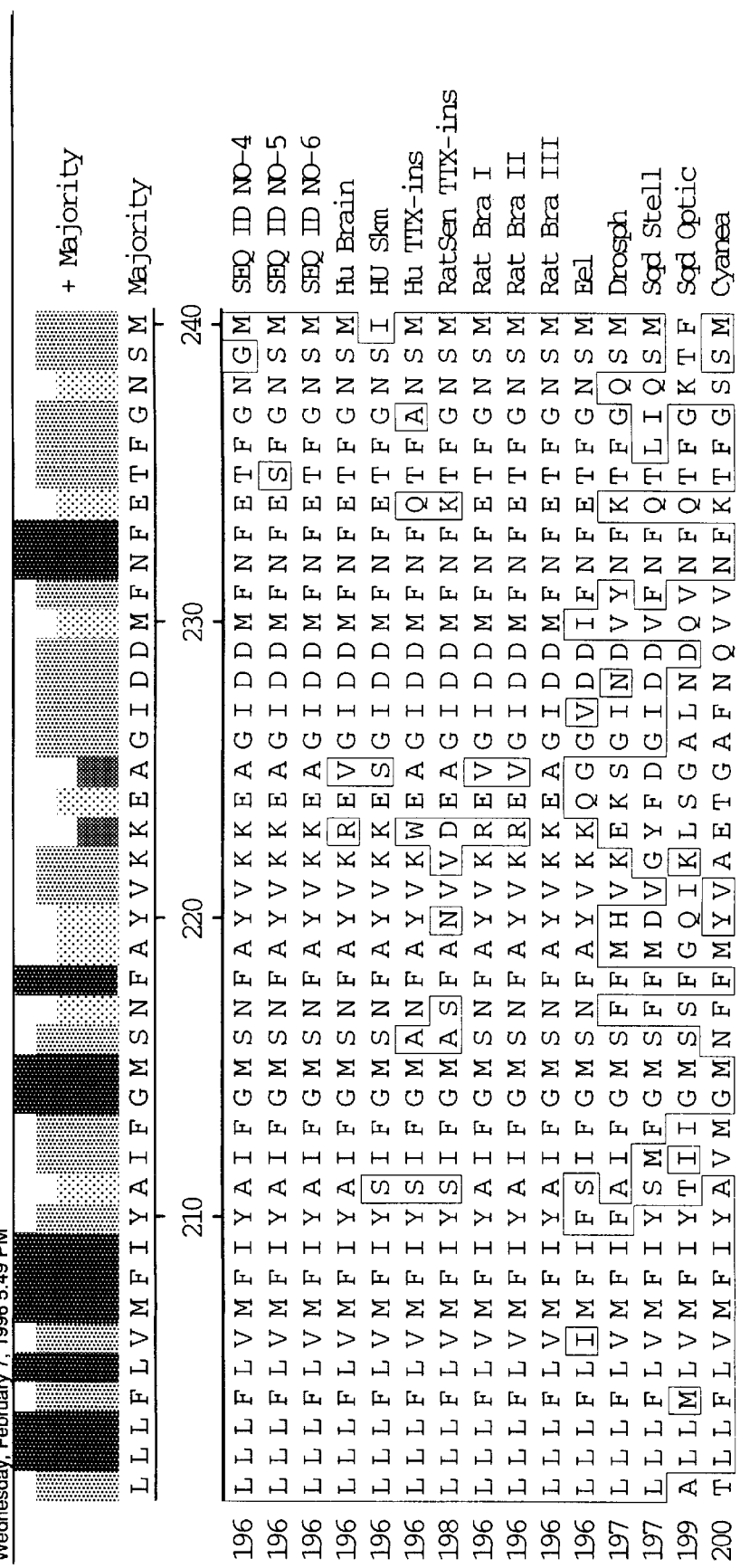
Figure 3H:
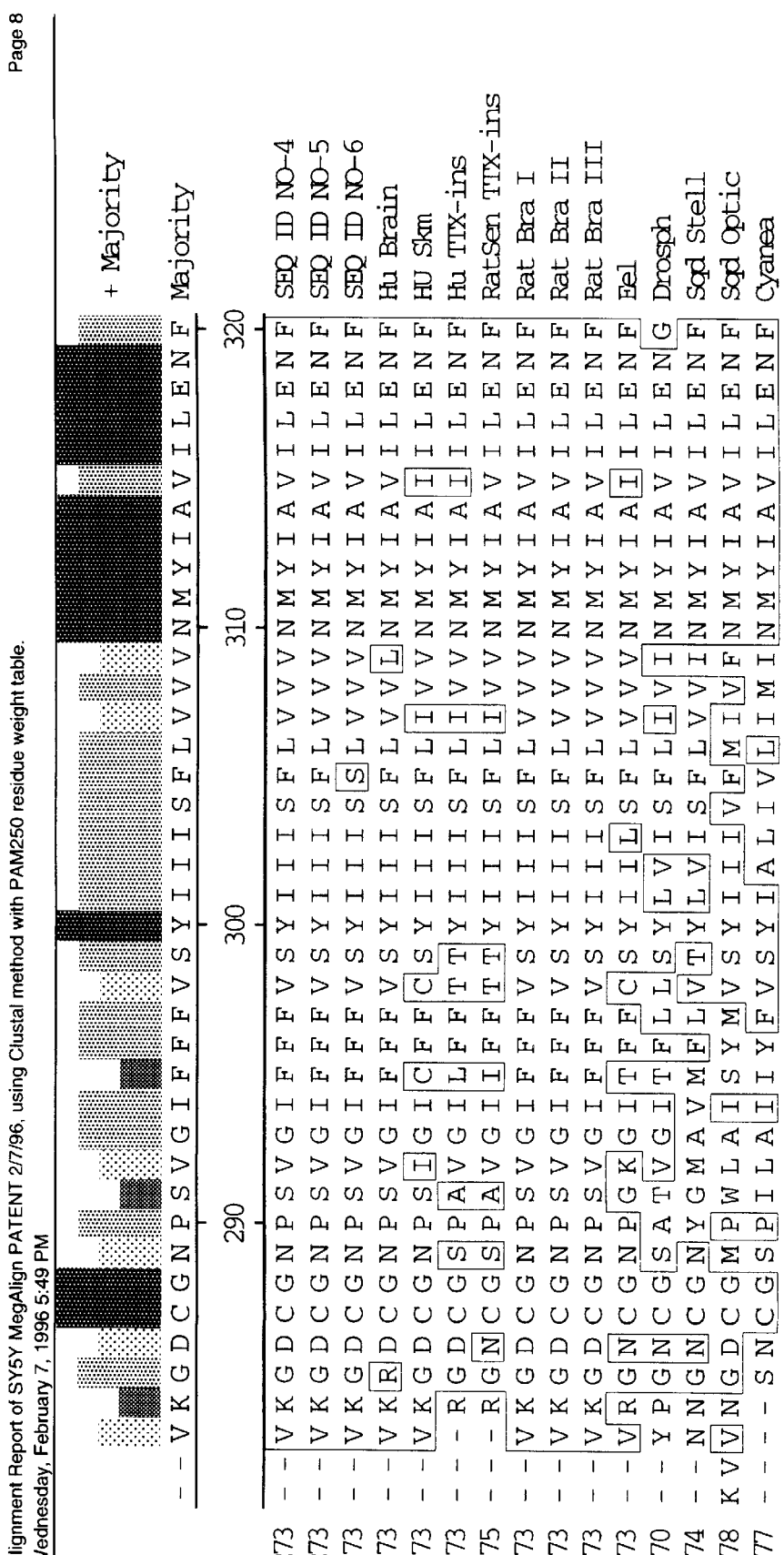

As used herein, the "nervous system" has two major divisions: the "central nervous system" and the "peripheral nervous system". The central nervous system contains the brain and nerve cord (also called the spinal cord), which lie in the midline of the body where the brain is protected by the skull and the nerve cord is protected by the vertebrae. The peripheral nervous system, as used herein, includes the somatic division (voluntary; to skeletal muscles, skin, joints, etc.) and the autonomic or visceral division (involuntary; to smooth muscles, cardiac muscle, glands), which contain all the cranial and spinal nerves. These peripheral nerves project out to the sides of the central nervous system. Peripheral nerve cells are the cells which make up the peripheral nervous system.

As also used herein, the term "isolated" when used in conjunction with a nucleic acid molecule refers to: 1) a nucleic acid molecule which has been separated from an organism in a substantially purified form (i.e. substantially free of other substances originating from that organism), or 2) a nucleic acid molecule having the same nucleotide sequence but not necessarily separated from the organism (i.e. synthesized nucleic acid molecules). The term "isolated" when used in conjunction with a channel refers to a channel encoded by such an "isolated" nucleic acid molecule, generally expressed in a membrane, such as a membrane of an organelle or a plasma membrane of a cell, or a synthetic lipid bilayer membrane. The expressed "isolated" channel has the pharmacological properties of a functional sodium channel.

As further used herein, the term "corresponding to" when used in conjunction with a SEQ ID NO for a nucleotide sequence refers to a nucleotide sequence which is substantially the same nucleotide sequence, or derivatives thereof (such as deletion and hybrid variants thereof, splice variants thereof, etc.). Nucleotide additions, deletions, and/or substitutions, such as those which do not affect the translation of the DNA molecule, are within the scope of a nucleotide sequence corresponding to a particular nucleotide sequence (i.e. the amino acid sequence encoded thereby remains the same). Such additions, deletions, and/or substitutions can be, for example, point mutations made according to methods known to those skilled in the art. It is also possible to substitute a nucleotide(s) which alters the amino acid sequence encoded thereby, where the amino acid substituted is a conservative substitution or where amino acid homology is conserved. It is also possible to have minor nucleotide additions, deletions, and/or substitutions which do not alter the function of the resulting VGSC. Similarly, the term "corresponding to" when used in conjunction with a SEQ ID NO for an amino acid sequence refers to an amino acid sequence which is substantially the same amino acid sequence or derivatives thereof. Amino acid additions, deletions, and/or substitutions which do not negate the ability of the resulting protein to form a functional sodium channel are within the scope of an amino acid sequence corresponding to a particular amino acid sequence. Such additions, deletions, and/or substitutions can be, for example, the result of point mutations in the DNA encoding the amino acid sequence, such point mutations made according to methods known to those skilled in the art. Substitutions may be conservative substitutions of amino acids. As used herein, two amino acid residues are conservative substitutions of one another where the two residues are of the same type. In this regard, for purposes of the present invention, proline, alanine, glycine, serine, and threonine, all of which are neutral, weakly hydrophobic residues, are of the same type. Glutamine, glutamic acid, asparagine, and aspartic acid, all of which are acidic, hydrophilic residues, are of the same type. Another type of residue is the basic, hydrophilic amino acid residue, which include histidine, lysine, and arginine. Leucine, isoleucine, valine, and methionine, all of which are hydrophobic, aliphatic amino acid residues, form yet another type of residue. Yet another type of residue consists of phenylalanine, tyrosine, and tryptophan, all of which are hydrophobic, aromatic residues. The function of the encoded sodium channel can be assayed for according to methods known in the art, such as by patch or voltage clamp analysis of expression in Xenopus oocytes (see Patton et al. 1992, Taglialatela et al. 1992, and Stuhmer 1989 for a general discussion of patch or voltage clamp analysis of expression of ion channels in Xenopus oocytes).

The subject invention provides an isolated nucleic acid molecule encoding a voltage gated sodium channel (VGSC) of a peripheral nerve, preferably a human peripheral nerve. The nucleic acid molecule can be deoxyribonucleic acid (DNA) or ribonucleic acid (RNA, including messenger RNA or mRNA), genomic or recombinant, biologically isolated or synthetic.

The DNA molecule can be a cDNA molecule, which is a complementary DNA copy of a messenger RNA (mRNA) encoding the VGSC. In one embodiment, the DNA encoding a VGSC includes a nucleotide sequence corresponding to SEQ ID NO:1 (which encodes an amino acid sequence having SEQ ID NO:4). In another embodiment, the DNA includes a nucleotide sequence corresponding to SEQ ID NO:2 (which encodes an amino acid sequence having SEQ ID NO:5), and in a further embodiment the DNA includes a nucleotide sequence corresponding to SEQ ID NO:3 (which encodes an amino acid sequence having SEQ ID NO:6). SEQ ID NOs 1, 2, and 3 are nucleotide sequences which are continuous portions of DNA molecules encoding entire VGSCs; accordingly, each VGSC "includes" the sequence shown. Each encoded entire VGSC is expected to be about 6500 bp, thus the subject invention provides about 15% of the nucleotide sequence of an entire voltage gated sodium channel of peripheral nerve. These sequences (SEQ ID NOs 1, 2 and 3) can readily be used to determine the sequences of the corresponding entire VGSCs, by the methods presented in Example II below.

The invention also provides an antisense nucleic acid molecule that is complementary to the mRNA encoding the VGSC, or a fragment thereof, or 5' and/or 3' untranslated regions which contain promoters and/or other regulatory and message stability domains thereof. Antisense molecules can be complementary to the entire or partial RNA molecule encoding the VGSC. Suitable fragments are capable of hybridizing to the mRNA encoding the entire molecule, and preferably consist of at least 10–15 nucleotides.

Antisense nucleic acid molecules can be RNA or single-stranded DNA. These antisense molecules and fragments thereof can be used to shut off an endogenous cellular gene encoding a VGSC of peripheral nerve, by introducing into cells an RNA or single-stranded DNA molecule that is complementary to the mRNA of the VGSC (i.e. by introducing an antisense molecule). The antisense molecule can base-pair with the mRNA of the VGSC, preventing translation of the mRNA into protein. Thus, an antisense molecule to the VGSC of peripheral nerve can prevent translation of mRNA encoding the VGSC into a functional sodium channel protein.

More particularly, an antisense molecule complementary to mRNA encoding a VGSC of peripheral nerve, or a fragment thereof, can be used to decrease expression of a functional VGSC of a peripheral nerve cell. A cell with a first level of expression of a functional VGSC of a peripheral nerve cell is first selected, and then the antisense molecule is introduced into the cell. The antisense molecule blocks expression of functional VGSCs of a peripheral nerve cell, resulting in a second level of expression of a functional VGSC of a peripheral nerve cell in the cell. The second level is less than the initial first level.

Antisense molecules can be introduced into cells by any suitable means. Suitable cells include Xenopus oocytes which are useful host cells for studying the expression of the encoded sodium channel, and various mammalian cells, including but not limited to peripheral nerve cells. In one embodiment, the antisense RNA molecule is injected directly into the cellular cytoplasm, where the RNA interferes with translation. A vector may also be used for introduction of the antisense molecule into a cell. Such vectors include various plasmid and viral vectors, including bacteriophage vectors. For a general discussion of antisense molecules and their use, see Han et al. 1991 and Rossi 1995.

The invention further provides a ribozyme having a recognition sequence complementary to the mRNA encoding the VGSC of peripheral nerve, or complementary to a fragment of the mRNA. Ribozymes not only complex with target sequences via complementary antisense sequences, but also hydrolyze or cleave the target site.

Introduction and/or expression of a ribozyme in a cell can inhibit gene expression (such as the expression of a VGSC of peripheral nerve). More particularly, a ribozyme having a recognition sequence complementary to mRNA encoding a VGSC of peripheral nerve, or complementary to a fragment thereof, can be used to decrease expression of a functional VGSC of a peripheral nerve cell. A cell with a first level of expression of a functional VGSC of a peripheral nerve cell is first selected, and then the ribozyme is introduced into the cell. Expression of the ribozyme in the cell decreases expression of a functional VGSC of a peripheral nerve cell in the cell, because mRNA encoding the VGSC is cleaved and cannot be transcribed.

Ribozymes can be introduced into cells by any suitable means. Suitable cells include Xenopus oocytes which are useful host cells for studying the expression of the encoded sodium channel, and various mammalian cells, including but not limited to peripheral nerve cells. In one embodiment, the ribozyme is injected directly into the cellular cytoplasm, where the ribozyme cleaves the mRNA and thereby interferes with translation. A vector may be used for introduction of the ribozyme into a cell. Such vectors include various plasmid and viral vectors, including bacteriophage vectors (note that the DNA encoding the ribozyme does not need to be "incorporated" into the genome of the host cell; it could be expressed in a host cell infected by a viral vector, with the vector expressing the ribozyme, for instance). For a general discussion of ribozymes and their use, see Sarver et al. 1990, Chrisey et al. 1991, Rossi et al. 1992, Christoffersen et al. 1995, and Marschall et al. 1994.

The nucleic acid molecules of the subject invention can be expressed in suitable host cells using conventional techniques. Any suitable host and/or vector system can be used to express the VGSCs. These include, but are not limited to, eukaryotic hosts such as mammalian cells (i.e., Hela cells, Cv-1 cells, COS cells), amphibian cells (i.e., Xenopus oocytes), and insect cells (i.e., Sf9 cells), as well as prokaryotic cells such as *Escherichia coli* and *Bacillus subtilis*.

Techniques for introducing the nucleic acid molecules into the host cells may involve the use of expression vectors which comprise the nucleic acid molecules. These expression vectors (such as plasmids and viruses; viruses including bacteriophage) can then be used to introduce the nucleic acid molecules into suitable host cells. For example, sodium channel expression is often studied in Xenopus oocytes. DNA encoding the VGSC can be injected into the oocyte nucleus or transformed into the oocyte using a suitable vector, or mRNA encoding the VGSC can be injected directly into the oocyte, in order to obtain expression of a functional VGSC in the oocyte. It may be beneficial when expressing the sodium channels of the subject invention in Xenopus oocytes to coexpress a nucleic acid molecule encoding a tipE protein (Feng et al. 1995). TipE has been found to greatly enhance functional expression of para locus sodium channels in Xenopus oocytes (Feng et al. 1995).

Various methods are known in the art for introducing nucleic acid molecules into host cells. One method is microinjection, in which DNA is injected directly into the nucleus of cells through fine glass needles (or RNA is injected directly into the cytoplasm of cells). Alternatively, DNA can be incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA). DNA can also be incorporated into artificial lipid vesicles, liposomes, which fuse with the cell membrane, delivering their contents directly into the cytoplasm. In an even more direct approach, used primarily with plant cells and tissues, DNA is absorbed to the surface of tungsten microprojectiles and fired into cells with a device resembling a shotgun.

Several of these methods, microinjection, electroporation, and liposome fusion, have been adapted to introduce proteins into cells. (For review, see Mannino and Gould-Fogerite 1988, Shigekawa and Dower 1988, Capecchi 1980, and Klein et al. 1987).

Further methods for introducing nucleic acid molecules into cells involve the use of viral vectors. Since viral growth depends on the ability to get the viral genome into cells, viruses have devised clever and efficient methods for doing it. The earliest viral vectors, based on the monkey tumor virus SV40, simply substituted some of the viral genes with the foreign gene. These recombinant molecules, prepared as bacterial plasmids, were transfected into monkey cells together with a second plasmid that supplied the missing viral genes. Once inside the cells, viral gene products produced from the two plasmids cooperate to replicate both plasmids and package each into virus particles. The virus stock that emerges from the cell is a mixture of two viruses, each of which is by itself defective (that is, it cannot replicate on its own because it is missing necessary viral genes). Nevertheless, this virus stock can then be used to infect new cells, efficiently introducing and expressing the foreign gene in the recipient cells.

A hybrid method that uses transfection to get DNA into cells and a viral protein to replicate it once inside is now commonly used for high-level production of protein from a cloned gene. This procedure uses a cell line, COS cells, carrying a stably integrated portion of the SV40 genome. These cells produce the viral T antigen protein, which triggers replication of viral DNA by binding to a DNA sequence termed the origin of replication. The foreign gene to be expressed is cloned into a plasmid that carries the SV40 origin of replication. After transfection into COS cells, the plasmid is replicated to a very high number of copies, increasing the expression level of the foreign gene.

Use of SV-40-based viral vectors is limited for a number of reasons: they infect only monkey cells, the size of foreign gene that can be inserted is small, and the genomes are often rearranged or deleted. Other viral vectors are more commonly used now, either because they can infect a wider range of cells or because they accept a wider range of foreign genes. Vaccinia virus is a large DNA-containing virus that replicates entirely in the cytoplasm. Early vaccinia vectors incorporated the foreign gene directly into a nonessential region of the viral genome. Recombinant viruses are viable and upon infection transcribe the foreign gene from a nearby viral promoter. Because the viral genome is large (185,000 bp), foreign genes cannot be inserted into vaccinia by standard recombinant DNA methods; instead, it must be done by recombination inside cells, a cumbersome and lengthy procedure. A more versatile vaccinia expression system uses a ready-made recombinant virus that expresses a bacteriophage RNA polymerase. The gene to be expressed is simply cloned into a plasmid carrying a bacteriophage promoter. The plasmid is transfected into cells that have been previously infected with the vaccinia virus that expresses the RNA polymerase. The gene on the plasmid is efficiently transcribed by the bacteriophage polymerase, accounting for up to 30 percent of the RNA in the cell. An additional feature of vaccinia virus infection is that the virus shuts down host cell protein synthesis so that viral mRNA (and mRNA from the plasmid) are preferentially translated into protein.

Another virus widely used for protein production is an insect virus, baculovirus. Baculovirus attracted the attention of researchers because during infection, it produces one of its structural proteins (the coat protein) to spectacular levels. If a foreign gene were to be substituted for this viral gene, it too ought to be produced at high level. Baculovirus, like vaccinia, is very large, and therefore foreign genes must be placed in the viral genome by recombination. To express a foreign gene in baculovirus, the gene of interest is cloned in place of the viral coat protein gene in a plasmid carrying a small portion of the viral genome. The recombinant plasmid is cotransfected into insect cells with wild-type baculovirus DNA. At a low frequency, the plasmid and viral DNAs recombine through homologous sequences, resulting in the insertion of the foreign gene into the viral genome. Virus plaques develop, and the plaques containing recombinant virus look different because they lack the coat protein. The plaques with recombinant virus are picked and expanded. This virus stock is then used to infect a fresh culture of insect cells, resulting in high expression of the foreign protein. For a review of baculovirus vectors, see Miller 1989.

All of the viruses discussed above are lytic viruses, in that they enter cells, take over, replicate massively, and get out, killing the cell in the process. So these vectors cannot be used to introduce a gene into cells in a stable fashion. This task can be performed by retroviruses. Retroviruses are RNA viruses with a life cycle quite different from that of the lytic viruses. When they infect cells, their RNA genomes are converted to a DNA form (by the viral enzyme reverse transcriptase). The viral DNA is efficiently integrated into the host genome, where it permanently resides, replicating along with host DNA at each cell division. This integrated provirus steadily produces viral RNA from a strong promoter located at the end of the genome (in a sequence called the long terminal repeat or LTR). This viral RNA serves both as mRNA for the production of viral proteins and as genomic RNA for new viruses. Viruses are assembled in the cytoplasm and bud from the cell membrane, usually with little effect on the cell's health. Thus, the retrovirus genome becomes a permanent part of the host cell genome, and any foreign gene placed in a retrovirus ought to be expressed in the cells indefinitely.

Retroviruses are therefore attractive vectors because they can permanently express a foreign gene in cells. Moreover, they can infect virtually every type of mammalian cell, making them exceptionally versatile. Because of their versatility, retroviruses are also the vector of choice for gene therapy. In the design and use of retroviral vectors, the vectors usually contain a selectable marker as well as the foreign gene to be expressed. Most of the viral structural genes are gone, so these vectors cannot replicate as viruses on their own. To prepare virus stocks, cloned proviral DNA is transfected into a packaging cell. These cells usually contain an integrated provirus with all its genes intact, but lacking the sequence recognized by the packaging apparatus. Thus, the packaging provirus produces all the proteins required for packaging of viral RNA into infectious virus particles but it cannot package its own RNA. Instead, RNA transcribed from the transfected vector is packaged into infectious virus particles and released from the cell. The resulting virus stock is termed helper-free because it lacks wild-type replication-competent virus. This virus stock can be used to infect a target cell culture. The recombinant genome is efficiently introduced, reverse-transcribed into DNA (by reverse transcriptase deposited in the virus by the packaging cells), and integrated into the genome. Thus, the cells now express the new virally introduced gene, but they never produce any virus, because the recombinant virus genome lacks the necessary viral genes. For a review of retrovirus vectors, see Cepko 1988, and Eglitis and Anderson 1988.

Another viral vector is adenovirus, reviewed by Berkner 1988. Still another viral vector is herpesvirus, reviewed by Latchman 1994.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures in the art, as described by Sambrook et al., *Molecular Cloning: A Laboratory Manual*, Cold Springs Laboratory, Cold Springs Harbor, N.Y. (1987).

Host cells into which the nucleic acid encoding the VGSC has been introduced can be used to produce (i.e. to functionally express) the voltage gated sodium channel.

Having identified the nucleic acid molecules encoding VGSCs and methods for expressing functional channels encoded thereby, the invention further provides a method of screening a chemical agent for the ability of the chemical agent to modify sodium channel function. The method comprises introducing a nucleic acid molecule encoding the VGSC into a host cell, and expressing the VGSC encoded by the molecule in the host cell. The expression results in the formation and expression of a functional VGSC in the membrane of the host cell. The cell is then exposed to a chemical agent and evaluated to determine if the chemical agent modifies the function of the VGSC. From this evaluation, chemical agents effective in altering the function of the sodium channels can be found. Such agents may be local anesthetics, general anesthetics, neurotoxic agents, or neurotrophic agents, for example. Chemical agents may also be identified which block or alter the function of sodium channels of sympathetic nerves to ameliorate cardiac arythmias and/or to reduce blood pressure, or which block the function of neuronal sodium channels to ameliorate ischemic damage, which can be useful in stroke therapy or epilepsy (see for example, Taylor 1993).

The nucleic acid molecules of the subject invention can also be used as probes or as primers in techniques such as polymerase chain reaction (PCR) cloning and colony/plaque hybridization, to obtain DNA encoding other VGSCs. Specific primers or probes derived from SEQ ID NOs 1, 2 or 3 can be used to prime DNA synthesis and PCR amplification, as well as to identify colonies containing cloned DNA encoding a member of the VGSC family using known methods (see Innis et al. 1990).

For example, in general when using primers derived from sequences for amplification, one skilled in the art will recognize that by employing high stringency conditions, such as, for example, annealing at 50–60° C., sequences which are greater than 75% homologous at the primer may be amplified. By employing lower stringency conditions, such as, for example, annealing at 35–37° C., sequences which are greater than 40–50% homologous at the primer may be amplified. These conditions and % homologies are examples only and are not limiting.

Also, in general, when using DNA probes derived from sequences for colony/plaque hybridization, one skilled in the art will recognize that by employing high stringency conditions, such as, for example, hybridization at 50–65° C., 5× SSPC, 50% formamide, wash at 50–65° C., 0.5× SSPC, sequences having regions which are greater than 90% homologous at the probe may be obtained, and by employing lower stringency conditions, such as, for example, hybridization at 35–37° C., 5× SSPC, 40–45% formamide, wash at 42° C., SSPC, sequences having regions which are greater than 35–45% homologous at the probe may be obtained. These conditions and % homologies are examples only and are not limiting.

More particularly, in one embodiment, the method comprises selecting a DNA molecule encoding a VGSC of a peripheral nerve cell, or a fragment thereof, the DNA molecule having a nucleotide sequence selected from the group consisting of SEQ ID NO:1, SEQ ID NO:2, and SEQ ID NO:3, and designing an oligonucleotide probe for a VGSC based on SEQ ID NO:1, SEQ ID NO:2 or SEQ ID NO:3. A genomic or cDNA library of an organism is then probed with the oligonucleotide probe, and clones are obtained from the library that are recognized by the oligonucleotide probe, so as to obtain DNA encoding another VGSC.

In a further embodiment, the method comprises selecting a DNA molecule encoding a VGSC of a peripheral nerve cell, the DNA molecule having a nucleotide sequence selected from the group consisting of SEQ ID NO:1, SEQ ID NO:2, and SEQ ID NO:3. Degenerate oligonucleotide primers are designed based on SEQ ID NO:1, SEQ ID NO:2 or SEQ ID NO:3, and are utilized in a polymerase chain reaction (PCR) on a DNA sample to be screened for VGSCs. Resulting PCR amplification products can be sequenced to identify any homologous DNA encoding a VGSC from the DNA sample.

Various modifications of the nucleic acid and amino acid sequences disclosed herein are covered by the subject invention. These varied sequences still encode a functional VGSC. The invention thus further provides an isolated nucleic acid molecule encoding a VGSC of a peripheral nerve cell, the nucleic acid molecule encoding a first amino acid sequence which includes a second amino acid sequence having at least 95% amino acid identity to a third amino acid sequence. In one embodiment, the third amino acid sequence is as shown in SEQ ID NO:4; in another embodiment, the third amino acid sequence is as shown in SEQ ID NO:5; and in a still further embodiment, the third amino acid sequence is as shown in SEQ ID NO:6.

The invention further provides isolated voltage gated sodium channels of peripheral nerve cells. In one embodiment, the peripheral nerve cell is a human peripheral nerve cell. The voltage gated sodium channels of the subject invention can be, for example, from the human neuroblastoma cell line designated SH-SY5Y. The SH-SY5Y cells are a cloned subline. The name of the mother uncloned cell line is SK-N-SH. SK-N-SH cells can be purchased from ATCC (the American Type Culture Collection, 12301 Parklawn Drive, Rockville, Md. 20852). The cloned subline SH-SY5Y is described by Biedler et al. 1978. In one embodiment, the VGSC is encoded by an amino acid sequence which includes SEQ ID NO:4. In a further embodiment, the VGSC is encoded by an amino acid sequence which includes SEQ ID NO:5, and in another embodiment by one which includes SEQ ID NO:6.

A variety of methodologies known in the art can be utilized to obtain an isolated VGSC according to the subject invention. In one method, the channel protein is purified from tissues or cells which naturally produce the channel protein. One skilled in the art can readily follow known methods for isolating proteins in order to obtain a member of the VGSC protein family, free of natural contaminants. These include, but are not limited to, immunochromatography, HPLC, size-exclusion chromatography, ion-exchange chromatography, and immunoaffinity chromatography. In another embodiment, a member of the VGSC family can be purified from cells which have been altered to express the channel protein. As used herein, a cell is said to be "altered to express the channel protein" when the cell, through genetic manipulation, is made to produce the channel protein which it normally does not produce or which the cell normally produces at low levels. One skilled in the art can readily adapt procedures for introducing and expressing either genomic, cDNA or synthetic sequences into either eukaryotic or prokaryotic cells in order to generate a cell which produces a member of the VGSC family utilizing the sequences disclosed herein.

A VGSC as defined herein includes molecules encoding VGSCs having a portion that has at least 95% amino acid identity to SEQ ID NO:4, or to SEQ ID NO:5, or to SEQ ID NO:6.

Antibodies can be raised to the voltage gated sodium channel. Antibodies of the subject invention include polyclonal antibodies and monoclonal antibodies capable of binding to the channel protein, as well as fragments of these antibodies, and humanized forms. Humanized forms of the antibodies of the subject invention may be generated using one of the procedures known in the art such as chimerization or Complementarity Determining Region (CDR) grafting. Fragments of the antibodies of the present invention include, but are not limited to, the Fab, the Fab2, and the Fd fragments.

The invention also provides hybridomas which are capable of producing the above-described antibodies. A hybridoma is an immortalized cell line which is capable of secreting a specific monoclonal antibody.

In general, techniques for preparing polyclonal and monoclonal antibodies as well as hybridomas capable of producing the desired antibody are well known in the art (see Campbell 1984 and St. Groth et al. 1980). Any animal (mouse, rabbit, etc.) which is known to produce antibodies can be immunized with the antigenic channel protein (or an antigenic fragment thereof). Methods for immunization are well known in the art. Such methods include subcutaneous or interperitoneal injection of the protein. One skilled in the art will recognize that the amount of the channel protein used for immunization will vary based on the animal which is immunized, the antigenicity of the protein, and the site of injection.

The protein which is used as an immunogen may be modified or administered in an adjuvant in order to increase the protein's antigenicity. Methods of increasing the antigenicity of a protein are well known in the art and include, but are not limited to, coupling the antigen with a heterologous protein (such as a globulin or beta-galactosidase) or through the inclusion of an adjuvant during immunization.

For monoclonal antibodies, spleen cells from the immunized animals are removed, fused with myeloma cells, such as SP2/O-Ag 15 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al. 1988).

Hybridomas secreting the desired antibodies are cloned and the class and subclass are determined using procedures known in the art (Campbell 1984).

For polyclonal antibodies, antibody containing antisera is isolated from the immunized animal and is screened for the presence of antibodies with the desired specificity using one of the above-described procedures.

The present invention further provides the above-described antibodies in detectably labeled form. Antibodies can be detectably labeled through the use of radioisotopes, affinity labels (such as biotin, avidin, etc.), enzymatic labels (such as horseradish peroxidase, alkaline phosphatase, etc.), fluorescent labels (such as FITC or rhodamine, etc.), paramagnetic atoms, etc. Procedures for accomplishing such labeling are well known in the art, for example see Sternberger et al. 1970, Bayer et al. 1979, Engval et al. 1972, and Goding 1976).

The labeled antibodies or fragments thereof of the present invention can be used for in vitro, in vivo, and in situ assays to identify cells or tissues which express a VGSC, to identify samples containing the VGSC proteins, or to detect the presence of a VGSC in a sample. More particularly, the antibodies or fragments thereof can thus be used to detect the presence of a VGSC in a sample, by contacting the sample with the antibody or fragment thereof. The antibody or fragment thereof binds to any VGSC present in the sample, forming a complex therewith. The complex can then be detected, thereby detecting the presence of the VGSC in the sample.

EXAMPLE 1

Materials and Methods
SH-SY5Y Human Neuroblastoma Cells

Neuroblastoma SH-SY5Y cells, which are derived from human peripheral nerves, have been shown to become electrical excitable when induced to undergo neuronal differentiation by exposure to retinoic acid (Brown et al. 1994). During neuronal differentiation the expression of functional calcium and sodium voltage dependent channels increases (presumably due to the increased expression of voltage gated sodium and calcium channels). Upon electrical stimulation, and in the presence of calcium channel blockers, these cells generate sodium-based action potentials. These sodium-based action potentials resemble those displayed by normal excitable tissues (with regard to their activation and inactivation kinetics), and are blocked by the highly selective sodium channel blocker tetrodotoxin.

In order to determine the identities of the voltage-gated sodium channels (VGSCs) expressed by these cells, an RT-PCR based isolation strategy was designed to amplify a reasonably sized segment of these very large genes.

SH-SY5Y cells were grown in media supplemented with 10% fetal calf serum for a period of three days to allow attachment. Those undergoing differentiation then had 10 $\mu$M retinoic acid added to their media. After five days of additional growth, the cells were harvested. Total RNA was transcribed into first strand cDNA using random primers and then subjected to two rounds of polymerase chain reaction (PCR) (the second nested), using two sets of highly degenerate oligonucleotide primers designed to recognize the most conserved nucleotide sequences which correspond to the highly conserved third and fourth transmembrane domains of the alpha subunit. Subsequent cloning of the PCR products, restriction analysis, and sequencing revealed three distinct sub-clones referred to as clone 3, clone 5, and clone 6 (one from undifferentiated and two from differentiated cells) which are unique, yet highly homologous to other members of the human VGSC family (see Tables 1 & 2).

Amino acid (aa) translation of the amplified cDNA demonstrated the expected high homology; specific motifs (see Table 3) expected are the IFM fast inactivation motif, the KKLGSKK (SEQ ID NO:22) consensus PKC phosphorylation site, the S4 voltage sensor [X-X-ARG or LYS]$_n$ repeat, the SS1–SS2 segments which contribute to the ion permeation pore, and proposed transmembrane domains IV-S1 through IV-S6. Therefore, these sequences represent new members of the human VGSC family isolated from peripheral nerve cells.

Methods for PCR Based Cloning Strategy

A PCR strategy was designed to sub-clone specific fragments of double-stranded (ds) cDNA representing VGSC message into plasmid constructs, to permit sequencing of these fragments, and identification of any novel members of the human voltage-gated sodium channel (VGSC) family.

SH-SY5Y Cell Culture

SH-SY5Y cells were plated at an initial density of 2×10⁵ cells per dish, in RPMI MEDIUM 1640 with L-glutamine (GIBCO, Grand Island, N.Y.) supplemented with 10% fetal calf serum (FCS). After 24 to 48 hrs of accommodation to the new substrate, the media was replaced, and that of the cells undergoing differentiation included retinoic acid (RA) at a concentration of 10 $\mu$M. After five days of culture (after addition of RA), cells of both treatment groups were washed with warm phosphate buffered saline, and then harvested by cell lysis in 2 mls of 4M Guanidinium thiocyanate.

RNA Isolation

Total cell RNA was isolated by the single-step RNA isolation method described in Ausubel et al. 1993. After phenol/chloroform extraction and ethanol precipitation, RNA was resolubilized in DEPC-treated water, and quantified by absorbance at 260 nm, and a 260/280 ratio of 1.8 or higher was the purity threshold for further use.

First Strand cDNA Synthesis

First strand cDNA synthesis was performed using the reagents from the cDNA Cycle® Kit (Invitrogen, San Diego, Calif.). In brief, 100 ng of total RNA was denatured by heat (65° for 10 mins.) and annealed with random hexamer primers. To this mix, RNase inhibitor (10 units), dNTPS [5mM], RT buffer and sodium pyrophosphate [4mM] were added, and this cocktail was incubated with AMV Reverse Transcriptase at 42° C. for one hour. After the first strand cDNA synthesis was complete, the reaction was stopped by placing the tubes on ice, until aliquots of the synthesis mix were used in the PCR amplification.

PCR Primers and Strategy

Highly degenerate oligonucleotide primers were designed by first aligning the amino acid sequences of various members of the VGSC family, in order to determine which amino acids are most highly conserved in this family. This analysis revealed that the 3rd–6th transmembrane segments of the 3rd and 4th transmembrane domains were the most highly conserved. Therefore, these regions were chosen for primer design. In addition, a nested PCR strategy was designed to increase the selectivity and specificity of this process. For the first round of amplification, the primers were: Forward (5')=SEQ ID NO:7: 5'GGGCGGCCGCGGITGGWTI-VAWRTHAATG 3' and Reverse (3')=SEQ ID NO:8: 5' GTTYTCIARRATIACIGCRATRTAC 3'. Once the anticipated ~1200 bp band was obtained, this material was subjected to a further round of PCR amplification using the "internal primer pair". These were: Forward (5')=SEQ ID NO:9: 5' GGGCGGCCGCGCGTNATHATIGAYAAYTTYAA 3' and Reverse (3')=SEQ ID NO:8: 5' GTTYTCIARRATI-ACIGCRATRTAC 3'. As used above, a nucleotide designated "I" refers to the synthetic nucleotide inosine which binds to A, T, C or G. In the SEQUENCE LISTING presented at the end of this Detailed Description, the nucleotide designated I above has been indicated as N for "other", in accordance with the rules for sequence listings.

PCR Optimization

The first strand cDNA from this step was amplified by PCR according to the following conditions. Degenerate forward and reverse primers (one each of the appropriate pair for each round of amplification, 50 pmols @/rxn), dNTPS (2.5 mM) and various buffers ( 60 mM Tris-HCl, 15mM $(NH_4)SO_4$, 3.5 mM $MgCl_2$, pH 8.5 (first reaction) or pH 9.0 (second reaction) (PCR Optimizer KIT, Invitrogen, San Diego, Calif.) were mixed with 1 μl of the first strand cDNA from the RT reaction, along with 2 units of Taq Polymerase (USB, Chicago, Ill.) in a final reaction volume of 50 μl. This reaction cocktail was overlayed with 20 μl of mineral oil, and kept at 4° C. until subjected to PCR amplification according to the following schedule for first round amplification: $1^{st}$ cycle, 92° C. for 4 mins., 37° C. for 2 mins., and 72° C. for 2 mins.; $2^{nd}$–$5^{th}$ cycles, 92° C. for 1.5 mins., 37° C. for 2 mins., and 72° C. for 2 mins.; $6^{th}$–$34^{th}$ cycles, 92° C. for 1.5 mins., 50° C. for 2 mins., and 72° C. for 2 mins.; and the $35^{th}$ cycle was 92° C. for 2 mins., 50° C. for 2 mins., and 72° C. for 10 mins., in order to "finish" incomplete strands. Second round amplification was performed according to the following schedule. $1^{st}$ cycle, 92° C. for 4 mins., 50° C. for 2 mins., and 72° C. for 2 mins.; $2^{nd}$–$34^{th}$ cycles, 92° C. for 1.5 mins., 50° C. for 2 mins., and 72° C. for 2 mins.; and the $35^{th}$ cycle was 92° C. for 2 mins., 50° C. for 2 mins., and 72° C. for 10 mins., to "finish" incomplete strands of this second round.

Cloning, Sequencing and Analysis of the PCR Products

PCR products from both rounds of amplification were directly cloned into the pCR_II vector according to the established protocols (TA Cloning® Kit, Invitrogen). The ligated plasmids were then introduced into OneSHOT modified *E. coli* cells by heat shock. After incubation at 37° C. for one hour with agitation, the transformed cells were plated onto LB plates (Kanamycin 50 μm/ml and X-gal) and appropriate colonies were picked by blue/white colony selection. These individual clones were amplified in LB plus Kanamycin 50 μM/ml, and plasmids were isolated by Wizard Mini-Prep Kit protocol (Promega, Madison, Wis.).

The PCR inserts were released from the isolated plasmids by Eco RI restriction enzyme digestion, to determine if the PCR inserts were of the appropriate lengths. The products of these restriction reactions were separated by agarose (1% in 1× TBE buffer) gel electrophoresis, and visualized with UV light by ethidium bromide staining, revealing inserts at or near the appropriate lengths (1200 bp for the first round of amplification, and ~930 bp for the second round of amplification).

Plasmids containing the appropriately sized fragments were further amplified and purified by Quiagen Plasmid Kit protocols (Quiagen, Chatsworth, Calif.). The PCR inserts were subjected to nucleic acid sequencing in both directions (Sequenase kit Ver. 2.0, USB, and New York State High Technology Center, Ithaca, N.Y.).

The derived DNA sequences were assembled by computer analysis (SeqMan, DNAstar, Madison, Wis.) and the identities of the assembled sequences were verified by non-redundant sequence comparison with the nucleic acid database of GENBANK, at the National Center for Biotechnology Information via BLAST server. In addition, the derived inframe amino acid sequences were also compared by the same Blast server, which again confirmed their identity as unique members of the VGSC family.

FIG. 3 shows the alignment of the amino acid sequences of clone 3 (C3 AA) (SEQ ID NO:4), clone 5 (C5 AA) (SEQ ID NO:5), and clone 6 (C6 AA) (SEQ ID NO:6) from human peripheral nerve according to the subject invention to various other sodium channels, including human brain (Hu Brain) (SEQ ID NO:10), human cardiac TTX insensitive sodium channel (Hu TTX-ins) (SEQ ID NO:11), human skeletal muscle (Hu Skm) (SEQ ID NO:12), rat brain isoform I (Rat Bra I) (SEQ ID NO:13), rat brain isoform II (Rat Bra II) (SEQ ID NO:14), rat brain isoform III (Rat Bra III) (SEQ ID NO:15), Eel (Eel) (SEQ ID NO:16), Squid optic nerve sodium channel (Sqd Optic) (SEQ ID NO:17), Squid stellate ganglion sodium channel (Sqd Stell) (SEQ ID NO:18), Drosophila sodium channel (Drosph) (SEQ ID NO:19) Rat Ser. TTX-ins (SEQ ID NO:23), and jellyfish sodium channel (Cyanea) (SEQ ID NO:20).

Figure 4A:
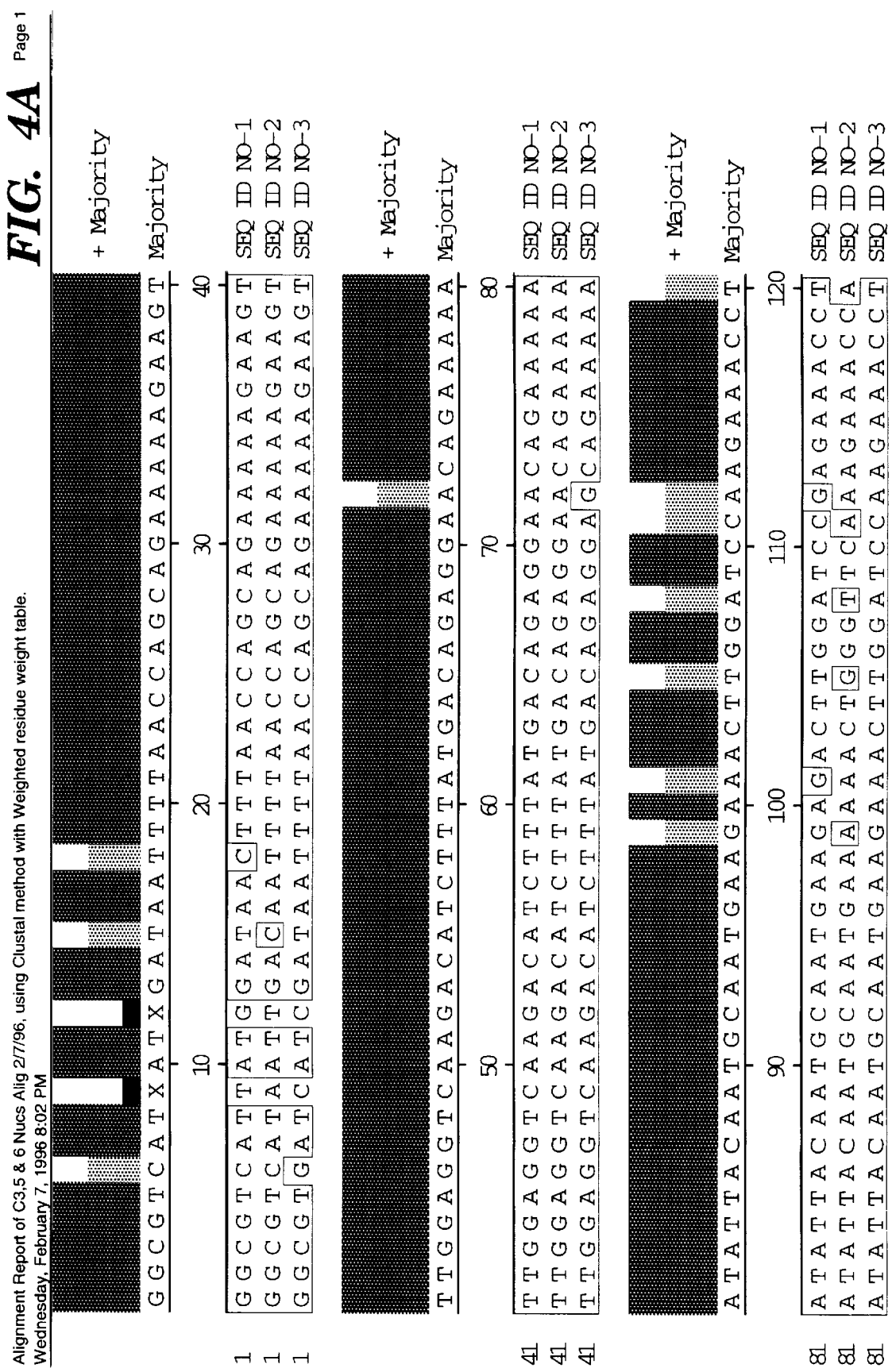

FIG. 4 shows the alignment of the amino acid and nucleotide sequences of the three sodium channels from human peripheral nerve according to the subject invention. SEQ ID NO:21 represents the "majority" amino acid sequence resulting from a comparison of amino acid SEQ ID NO:4 for clone 3, amino acid SEQ ID NO:5 for clone 5, and amino acid SEQ ID NO:6 for clone 6. The nucleotide sequences for clone 3 (SEQ ID NO:1), clone 5 (SEQ ID NO:2), and clone 6 (SEQ ID NO:3) are also shown.

EXAMPLE II cDNA Library Construction and Screening

Two cDNA Libraries were constructed, one from undifferentited SH-SY5Y and one from Differentiated SH-SY5Y cells. The differentiated cells were treated as before, after plating and attachment, 10 μm retinoic acid was included in the culture media, and the cells were cultured for another five days.

RNA Isolation for SH-SY5Y cells

RNA from the cultured cells was harvested according to the TRIZOL®™ reagent protocol. The culture media was removed by aspiration, and the cells were rinsed by several washes with 37° C. sterile phosphate buffered saline. Upon removal of the final wash, 3 mls of TRIZOL were added to each culture dish, and repeatedly pipetted up and down to ensure lysis of the cells. This rapid cellular lysis and denaturation of the endogenous RNAses is critical to the succces of the entire library, by ensuring a high proportion of full-length RNA.

After allowing the cellular mix/TRIZOL to stand for five minutes, 0.2 mls of chloroform/ml TRIZOL mix were added and vortexed. These solutions were centrifuged for mins, 10,000 G, at 4° C.. The clear supernatent contains the RNA, and was separated into another tube for subsequent ethanol precipitation, by adding 2.5 volumns of 100% ethanol and stored at −20° C. until further use.

mRNA Isolation

The solutions were centrifuged for 15 mins, at 10,000 G, at 4° C. The supernatents were removed by aspiration, and the resulting pellets were air dried, resolubilized in 100 μl of DEPC water, quantified by spectroscopy, and used in the Micro Fast Track mRNA isolation protocol. This protocol is based on oligo dT affinity matrix and a series of higher stringency salt buffers to selectively retain and elute highly pure mRNA.

cDNA Library Construction

The directional cDNA library was constructed according to the general guidelines of the GIBCO BRL Superscript™ Plasmid System for cDNA Synthesis and Cloning.

In brief, poly(A)+ mRNA was primed with a specially designed NOT 1 oligo dT primer-adaptor, and transcribed into first strand cDNA using Superscript™ reverse transcriptase. To improve the chances of a full length cDNA transcript, the reaction was run at 50° C., instead of 37° C. A trace amount of [alpha-$^{32}$P]dCTP was included in the reaction to monitor yield.

The RNA was digested away with RNAse H, and the synthesis of the second strand was self-primed (3' hairpin), permitting E. Coli DNA polymerase and ligase to synthesize the second strand. After a two hour incubation, T4 DNA polymerase was included to ensure the completeness of the second strand reaction.

At this point, the Sal 1 adaptors were ligated on to both ends in a blunt-ended reaction with T4 DNA Ligase.

These products were then cut with NOT1 restriction enzyme to permit directional cloning.

The double stranded products were then size selected over mini-columns to remove excess adaptors and cleaved ends.

After size selection and yield calculation by Cherenkov counting, the fractions were pooled and ligated into the Not1-Sal1 cut pSPORT plasmid vector.

After ligation into the vector, the intact vectors were electroporated into electrocompetent E. coli.

The efficiency of transformation was calculated by plating serial dilutions of a fraction of the cDNA library, and a separate fraction of control transformant, onto LB plates containing 100 µg/ml of Ampicillin. The number of colonies from each fraction were counted after 36 hours growth, providing the multiple for the total number of transformants of each pool.

cDNA Library Screening

Using the number of transformants per library determined above, a series of screening plates for each library were plated, such that 20,000–50,000 colonies grew per plate. In order to minimize the possibility of rearrangement of these large cDNA constructs (especially due to the number of "internal repeats" present in the VGSC), the cells were grown at 30° C.

The colonies were lifted and bound to Nytran Plus (S&S) positively charged nylon membranes, which were fixed by 10% SDS, alkaline denaturing solution, neutralizing solution, 2x SSC, dried, and cross linked by UV (Auto link [1200×100]. The membranes were then treated with Proteinase K to remove protein (and eliminate background). After washing in 1x SSC, filters were prehybridized (1x hybridization buffer—radiolabelled probe) for two hours at 65° C. During this time, the probe (random primed copies of the isolated PCR products of the individual SH-SY5Y VGSC clones) was precipitated and heat denatured (previously synthesized according to the Decaprime Kit protocol [Ambion]). After snap cooling, the probe was added to the hybridization buffer, and this mix was allowed to hybridize overnight at 65° C. The next day, the filters were subjected to a series of washes of increasing stringency (2–0.1xSSC, 0.2–0.1% SDS for 30 mins at 65° C. After the final wash, the filters were laid out on Saran Wrap in order and in the proper orientation, covered with Saran Wrap, and exposed overnight to X-Ray films (Kodak). After the appropriate exposure times (~12–48 hrs.), the films were developed, and any "hot colonies" were lifted from the original plates, mixed in LB and replated. The screening process was then repeated to further isolate the VGSC clones.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

VGSC FAMILY IDENTITY TABLES
VGSC NUCLEIC ACID IDENTETY

| SY5Y Fragment | | HUMAN Brain Accession # gb/M94055 | | HUMAN NeurEndo Accession # emb/X82835 | | HUMAN Brain Accession # gb/M91803 | | HUMAN Skel Musc Accession # gb/M81758 | | HUMAN Cardiac Accession # gb/M77235 | | HUMAN Heart/Uter Accession # gb/M91556 | |
|---|---|---|---|---|---|---|---|---|---|---|---|---|---|
| SEQ ID | NUCS | % Iden | Length | % Iden | Length | % Iden | Length | % Iden | Length | % Iden | Length | % Iden | Length |
| NO-1 | 930 | 90 | 930 | 85 | 923 | 87 | 812 | 74 | 924 | 73 | 788 | 68 | 921 |
| NO-2 | 930 | 92 | 930 | 90 | 913 | 91 | 814 | 73 | 921 | 74 | 764 | 70 | 910 |
| NO-3 | 930 | 90 | 930 | 85 | 915 | 87 | 803 | 74 | 916 | 72 | 789 | 68 | 914 |

TABLE 2

VGSC AMINO ACID IDENTITY

| SY5Y Fragment | | HUMAN Brain Accession # gp/M94055 | | HUMAN Brain Accession # pir/A46269 | | HUMAN NeurEndo Accession # gp/X82835 | | HUMAN Skel Musc Accession # sp/P35499 | | HUMAN Skel Musc Accession # gp/M81758 | | HUMAN Skel Musc Accession # gp/L04236 | |
|---|---|---|---|---|---|---|---|---|---|---|---|---|---|
| SEQ ID | AA | % Iden | Length | % Iden | Length | % Iden | Length | % Iden | Length | % Iden | Length | % Iden | Length |
| NO-4 | 310 | 91 | 310 | 91 | 310 | 85 | 310 | 80 | 310 | 80 | 310 | 80 | 310 |
| NO-5 | 310 | 93 | 310 | 92 | 310 | 86 | 310 | 81 | 310 | 81 | 310 | 81 | 310 |
| NO-6 | 310 | 92 | 310 | 91 | 310 | 85 | 310 | 80 | 310 | 80 | 310 | 80 | 310 |

These tables include selected human sequences from the VGSC family. Since the above are only partial sequences, the percentages reported by GENBANK cannot be considered to be exact, but only representative. Note that BLAST SERVER reports the precent identities only over those regions within the total SY5Y sequence which have reasonable identity.

TABLE 3

Amino Acid Structural Motif Summary

| Structural Motif | SEQ ID NO-4 | SEQ ID NO-5 | SEQ ID NO-6 |
|---|---|---|---|
| Transmembrane Segments IVS1–S6 | YES | YES | YES |
| Inactivation IFM | YES | YES | YES |
| PKC Consensus KKLGSKK | KRLGSEK | YES | YES |
| Voltage Sensor [X—X—R or K]$_n$ | YES | YES | YES |
| SS1–SS2 Segments | YES | YES | YES |
| Na+ Permeability A—X—X—D—G | A—X—X—G—G | YES | YES |
| Local Anesthetic I—I—I—S—F—L | YES | YES | I—I—I—S—S—L |
| TTX Binding A "1714" | YES | YES | YES |

Specitic amino acid substitutions of highly conserved motifs in the currently reported clones are illustrated above by an enlarged font. The R for K substitution in the PKC site is reasonable. However the acidic E for the basic K is a profound substitution, yet this is also seen in the Cyanea domain II. Na+ permeablilty may be affected by the G for D substitution in C3. Finally, at the local anesthetic binding region, the substituion of S (containing an aliphatic hydroxyl group) for the hydrophobic and aromatic F is also interesting.

LIST OF REFERENCES CITED

Agnew, W. S., *Nature,* 322:770–771 (1986).
Agnew, W. S., et al., *Proc Natl Acad Sci USA* 75:2606–2610 (1978).
Agnew, W. S., et al., *Biochem Biophys Res Comm* 92:860–866 (1980).
Alberts, B., et al., eds., *Molecular Biology of the Cell,* pp. 534–535, Garland Publishing, New York, N.Y. (1994).
Anderson, O. S. and Koepe, R. E., *Physiological Reviews* 72(4)Supplement: S89–S158 (1992).
Auld, V. J., et al., *Neuron* 1:449–461 (1988).
Ausubel, et al., *Current Protocols in Molecular Biology,* John Wiley & Sons Inc., New York, N.Y. (1993).
Barchi, R. L., Probing the Molecular Architecture of the Voltage-Dependent Sodium Channel in "The Molecular Biology of Receptors, Pumps, and Channels: Pharmacological Targets," ASPET Meeting Abstracts; (Aug. 1988).
Bayer, E. A., et al., *Meth Enzym* 62:308 (1979).
Berkner, K. L., *BioTechniques* 6:616–629 (1988).
Biedler, J. L., et al., *Cancer Res* 38:3751–3757 (1978).
Brown, N. A., et al., *British Journal of Pharmacology* 113(2):600–606 (1994).
Campbell, A. M., "Monoclonal Antibody Technology: Laboratory Techniques in Biochemistry and Molecular Biology", Elsevier Science Publishers, Amsterdam, The Netherlands (1984).
Capecchi, M., *Cell* 22:479–488 (1980).
Catterall, W. A., *Ann Rev Biochem* 55:953–985 (1986).
Catterall, W. A., *ISI Atlas of Science: Pharmacology* 190–195 (1988).
Catterall, W. A., *Science* 242:50–61 (1988a).
Catterall, W. A., *Physiological Reviews* 72 (4):S14–S48 (1992).
Cepko, C., *Neuron* 1:345–353 (1988).
Chrisey, L., et al., *Antisense Research and Development* 1(1):57–63 (1991).
Christoffersen, R. E. and Marr, J. J., *Journal of Medicinal Chemistry* 38(12):2023–2037 (1995).
Eglitis, M. A. and W. F. Anderson, *BioTechniques* 6:608–614 (1988).
Engval, E. et al., *Immunol* 109:129 (1972).
Feng, G., et al., *Cell* 82(6):1001–1011 (1995).
Goding, J. W., *J Immunol Meth* 13:215 (1976).
Goldin, A. L., et al., *Proc Natl Acad Sci USA* 83:7503–7507 (1986).
Greenblatt, R. E., et al., *FEBS* 193:125–134 (1985).
Guy, R. H., et al., *Proc Natl Acad Sci USA* 83:508–512 (1986).
Han, L., et al., *Proc Natl Acad Sci USA* 88:4313–4317 (1991).
Hartshorne, R. P., and Catterall, W. A., *J Biol Chem* 259:1667–1675 (1984).
Innis, et al., *PCR Protocols,* Academic Press, San Diego, Calif. (1990).
Kayano, T., et al., *FEBS Letters* 228:187–194 (1988).
Klein, T. M., et al., *Nature* 327:70–73 (1987).
Kraner, S. D., et al., *J Biol Chem* 260(10):6341–6347 (1985).
Latchman, D. S., *Mol Biotechnol* 2(2):179–195 (1994).
Lutz, et al., *Exp Cell Res* 175:109–124 (1988).
Mannino, R. J. and S. Gould-Fogerite, *BioTechniques* 6:682–690 (1988).
Marschall, P., et al., *Cell Mol Neurobiol* 14(5):523–538 (1994).
Messner, D. J., et al., *J Biol Chem* 261:14882 (1986).
Miller, L. K., *Bioessays* 11:91–95 (1989).
Noda, M., et al., *Nature* 312:5990 (1984).
Noda, M., et al., *Nature* 320:188–192 (1986a).
Noda, M., et al., *Nature* 322:826–828 (1986b).
Patton, D. E., et al., *Proc Natl Acad Sci USA* 89:10905–10909 (1992).
Rogart, R. B., U.S. Pat. No. 5,380,836, issued Jan. 10, 1995 entitled "Nucleic Acid Encoding Sodium Channel Protein".
Rossi, J. J., *British Medical Bulletin* 51(1) :217–225 (1995).
Rossi, J. J., et al., *AIDS Research and Human Retroviruses* 8(2):183–189 (1992).
Salkoff, L., et al., *Nucleic Acids Res* 15(20):8569–8572 (1987a).
Salkoff, L., et al., *Science* 237:744–749 (1987b).
Sambrook et al., *Molecular Cloning: A Laboratory Manual,* 2d Edition, Cold Spring Harbor Laboratory, Cold Spring Harbor, N.Y. (1989).
Sarver, N., et al., *Science* 247:1222–1225 (1990).
Shigekawa, K. and W. J. Dower, *BioTechniques* 6:742–751 (1988).
St. Groth, et al., *J Immunol Methods* 35:1–21 (1980).
Sternberger, L. A., et al., *J Histochem Cytochem* 18:315 (1970).
Suzuki, H., et al., *FEBS Letters* 228:195–200 (1988).
Stuhmer, W., et al., *Eur Biophys J* 14:131–138 (1987).
Stuhmer, W., et al., *Nature* 339:597–603 (1989).
Taglialatela, M., et al., *Biophys J* 61:78–82 (1992).
Tanaka, J. C., et al., *J Biol Chem* 258(12):7519–7526 (1983).
Taylor, C. P., *Trends Neurosci* 16:455–460 (1993).

What is claimed is:

1. An isolated nucleic acid molecule comprising a nucleotide sequence which encodes the amino acid sequence of SEQ ID NO: 4, SEQ ID NO: 5, or SEQ ID NO: 6.

2. The isolated nucleic acid molecule of claim 1 wherein said nucleic acid molecule encodes a protein or polypeptide comprising the amino acid sequence of SEQ ID NO: 4.

3. The isolated nucleic acid molecule of claim 1 wherein said nucleic acid molecule encodes a protein or polypeptide comprising the amino acid sequence of SEQ ID NO: 5.

4. The isolated nucleic acid molecule of claim 1 wherein said nucleic acid molecule encodes a protein or polypeptide comprising the amino acid sequence of SEQ ID NO: 6.

5. The isolated nucleic acid molecule of claim 1 wherein said nucleic acid molecule is deoxyribonucleic acid (DNA).

6. The isolated nucleic acid molecule of claim 5 wherein said DNA includes the nucleotide sequence of SEQ ID NO: 1.

7. The isolated nucleic acid molecule of claim 5 wherein said DNA includes the nucleotide sequence of SEQ ID NO: 2.

8. The isolated nucleic acid molecule of claim 5 wherein said DNA includes the nucleotide sequence of SEQ ID NO: 3.

9. The isolated nucleic acid molecule of claim 1 wherein said nucleic acid molecule is ribonucleic acid (RNA).

10. The isolated nucleic acid molecule of claim 1 wherein the nucleic acid molecule is isolated from a mammalian peripheral nerve cell library.

11. The isolated nucleic acid molecule of claim 10 wherein said mammalian peripheral nerve cell library is a human neuroblastoma cell library.

12. The isolated nucleic acid molecule of claim 11 wherein said human neuroblastoma cell library is a SH-SY5Y library.

13. A cell comprising the nucleic acid molecule of claim 1.

14. An expression vector comprising the nucleic acid molecule of claim 1.

15. The expression vector of claim 14 wherein said expression vector is selected from the group consisting of a plasmid and a virus.

16. The expression vector of claim 15 wherein said virus is a bacteriophage.

17. A cell comprising the expression vector of claim 14.

18. A method of producing a polypeptide, said method comprising:

introducing the nucleic acid molecule of claim 1 into a cell; and allowing the cell to express the nucleic acid molecule to produce the polypeptide in the cell.

19. The method of claim 18 wherein the cell is a Xenopus oocyte and the nucleic acid molecule is an mRNA molecule.

20. The method of claim 18 wherein the cell is a mammalian cell.

21. An isolated polypeptide comprising the amino acid sequence of SEQ ID NO: 4.

22. An isolated polypeptide comprising the amino acid sequence of SEQ ID NO: 5.

23. An isolated polypeptide comprising the amino acid sequence of SEQ ID NO: 6.

24. An isolated polypeptide fragment of a voltage gated sodium channel, wherein the isolated polypeptide fragment consists of the amino acid sequence of SEQ ID NO: 4, SEQ ID NO: 5, or SEQ ID NO: 6.

25. The isolated polypeptide fragment of claim 24, wherein the isolated polypeptide fragment consists of the amino acid sequence of SEQ ID NO: 4.

26. The isolated polypeptide fragment of claim 24, wherein the isolated polypeptide fragment consists of the amino acid sequence of SEQ ID NO: 5.

27. The isolated polypeptide fragment of claim 24, wherein the isolated polypeptide fragment consists of the amino acid sequence of SEQ ID NO: 6.

* * * * *

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
          (A) LENGTH: 930 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:1:

GGCGTCATTA TAGATAACTT TAACCAGCAG AAAAAGAAGT TTGGAGGTCA AGACATCTTT        60

ATGACAGAGG AACAGAAAAA ATATTACAAT GCAATGAAGA GACTTGGATC CGAGAAACCT       120

CAGAAACCCA TACCTCGCCC AGCAAACAAA TTCCAAGGAA TGGTCTTTGA TTTTGTAACC       180

AGACAAGTCT TTGATATCAG CATCATGATC CTCATCTGCT TCAACATGGT CACCATGATG       240

GTGGAAACGG ATGACCAGGG CAAATACATG ACCCTAGTTT TGTCCCGGAC CAACCTAGTG       300

TTCATTGTTC TGTTCACTGG AGAATTTGTG CTGAAGCTCG TCTCCCTCAG ACACCACTAC       360

TTCACTATAG GCTGGAACAT CTTTGACTTT GTGGTGGTGA TTCTCTCCAT TGTAGGTATG       420

TTTCTGGCTG AGATGATAGA AAAGTATTTT GTGTCCCCTA CCTTGTTCCG AGTGATCCGT       480

CTTGCCAGGA TTGGCCGAAT CCTACGTCTG ATCAAAGGAG CAAAGGGGAT CCGCACGCTG       540

CTCTTTGCTT TGATGATGTC CCTTCCTGCG TTGTTTAACA TCGGCCTCCT GCTCTTCCTG       600

GTCATGTTTA TCTATGCCAT CTTTGGGATG TCCAACTTTG CCTATGTAAA AAAGGAGGCT       660

GGAATTGATG ACATGTTCAA CTTTGAGACC TTTGGCAACG GCATGATCTG CTTGTTCCAA       720

ATTACAACCT CTGCTGGCTG GGGTGGATTG CTAGCACCTA TTCTTAATAG TGCACCACCC       780

GACTGTGACC CTGACACAAT TCACCCTGGC AGCTCAGTTA AGGGAGACTG TGGGAACCCA       840

TCTGTTGGGA TTTTCTTTTT TGTCAGTTAC ATCATCATAT CCTTCCTGGT TGTGGTGAAT       900

ATGTATATTG CCGTCATTCT CGAGAACTTT                                       930

(2) INFORMATION FOR SEQ ID NO:2:

(i) SEQUENCE CHARACTERISTICS:
          (A) LENGTH: 930 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:2:

GGCGTCATAA TTGACAATTT TAACCAGCAG AAAAAGAAGT TTGGAGGTCA AGACATCTTT        60

ATGACAGAGG AACAGAAAAA ATATTACAAT GCAATGAAAA AACTGGGTTC AAAGAAACCA       120

CAAAAACCCA TACCTCGACC TGCTAACAAA TTCCAAGGAA TGGTCTTTGA TTTTGTAACC       180

AAACAAGTCT TTGATATCAG CATCATGATC CTCATCTGCC TTAACATGGT CACCATGATG       240

GTGGAAACCG ATGACCAGAG TCAAGAAATG ACAAACATTC TGTACTGGAT TAATCTGGTG       300

TTCATTGTTC TGTTCACTGG AGAATTTGTG CTGAAGCTCG TCTCCCTCAG ACACTACTAC       360

TTCACTATAG GCTGGAACAT CTTTGACTTT GTGGTGGTGA TTCTCTCCAT TGTAGGTATG       420

```
TTTCTGGCTG AGATGATAGA AAAGTATTTT GTGTCCCCTA CCTTGTTCCG AGTGATCCGT      480

CTTGCCAGGA TTGGCCGAAT CCTACGTCTG ATCAAAGGAG CAAAGGGGAT CCGCACGCTG      540

CTCTTTGCTT TGATGATGTC CCTTCCTGCG TTGTTTAACA TCGGCCTCCT GCTCTTCCTG      600

GTCATGTTTA TCTATGCCAT CTTTGGGATG TCCAACTTTG CCTATGTTAA AAAGGAAGCT      660

GGAATTGATG ACATGTTCAA CTTTGAGTCC TTTGGCAACA GCATGATCTG CTTGTTCCAA      720

ATTACAACCT CTGCTGGCTG GGATGGATTG CTAGCACCTA TTCTTAATAG TGCACCACCC      780

GACTGTGACC CTGACACAAT TCACCCTGGC AGCTCAGTTA AGGGAGACTG TGGGAACCCA      840

TCTGTTGGGA TTTTCTTTTT TGTCAGTTAC ATCATCATAT CCTTCCTGGT TGTGGTGAAT      900

ATGTATATTG CCGTCATTCT CGAAAACTTT                                        930

(2) INFORMATION FOR SEQ ID NO:3:

(i) SEQUENCE CHARACTERISTICS:
        (A) LENGTH: 930 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GGCGTGATCA TCGATAATTT TAACCAGCAG AAAAAGAAGT TTGGAGGTCA AGACATCTTT       60

ATGACAGAGG AGCAGAAAAA ATATTACAAT GCAATGAAGA AACTTGGATC CAAGAAACCT      120

CAGAAACCCA TACCTCGCCC AGCAAACAAA TTCCAAGGAA TGGTCTTTGA TTTTGTAACC      180

AGACAAGTCT TTGATATCAG CATCGTGATC CTCATCTGCC TCAACATGGT CACCATGATG      240

GTGGAAACGG ATGACCAGGG CAAATACATG ACCCTAGTTT TGTCCCGGAT CAACCTAGTG      300

TTCATTGTTC TGTTCACTGG AGAATTTGTG CTGAAGCTCG TCTCCCTCAG ACACTACTAC      360

TTCACTATAG GCTGGAACAT CTTTGACTTT GTGGTGGTGA TTCTCTCCAT TGTAGGTATG      420

TTTCTGGCTG AGATGATAGA AAAGTATTTT GTGTCCCCTA CCTTGTTCCG AGTGATCCGT      480

CTTGCCAGGA TTGGCCGAAT CCTACGTCTG ATCAAAGGAG AAAGGGGATC CGCACCCTG      540

CTCTTTGCTT TGATGATGTC CCTTCCTGCG TTGTTTAACA TCGGCCTCCT GCTCTTCCTG      600

GTCATGTTTA TCTATGCCAT CTTTGGGATG TCCAACTTTG CCTATGTTAA AAAGGAAGCT      660

GGAATTGATG ACATGTTCAA CTTTGAGACC TTTGGCAACA GCATGATCTG CTTGTTCCAA      720

ATTACAACCT CTGCTGGCTG GGATGGATTG CTAGCACCTA TTCTTAATAG TGCACCACCC      780

GACTGTGACC CTGACACAAT TCACCCTGGC AGCTCAGTTA AGGGAGACTG TGGGAACCCA      840

TCTGTTGGGA TTTTCTTTTT TGTCAGTTAC ATCATCATAT CCTCCCTGGT TGTGGTGAAC      900

ATGTATATTG CCGTCATCCT CGAAAACTTT                                        930

(2) INFORMATION FOR SEQ ID NO:4:

(i) SEQUENCE CHARACTERISTICS:
        (A) LENGTH: 309 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:4:

Gly Val Ile Met Asp Asn Phe Asn Gln Gln Lys Lys Lys Phe Gly Gly
1               5                   10                  15
```

```
Gln Asp Ile Phe Met Thr Glu Glu Gln Lys Lys Tyr Tyr Asn Ala Met
            20                  25                  30

Lys Arg Leu Gly Ser Glu Lys Pro Gln Lys Pro Ile Pro Arg Pro Ala
            35                  40                  45

Asn Lys Phe Gln Gly Met Val Phe Asp Phe Val Thr Arg Gln Val Phe
 50                  55                  60

Asp Ile Ser Ile Met Ile Leu Ile Cys Phe Asn Met Val Thr Met Met
 65                  70                  75                  80

Val Glu Thr Asp Asp Gln Gly Lys Tyr Met Thr Leu Val Leu Ser Arg
                85                  90                  95

Thr Asn Leu Val Phe Ile Val Leu Phe Thr Gly Glu Phe Val Leu Lys
            100                 105                 110

Leu Val Ser Leu Arg His His Tyr Phe Thr Ile Gly Trp Asn Ile Phe
            115                 120                 125

Asp Phe Val Val Val Ile Leu Ser Ile Val Gly Met Phe Leu Ala Glu
            130                 135                 140

Met Ile Glu Lys Tyr Phe Val Ser Pro Thr Leu Phe Arg Val Ile Arg
145                 150                 155                 160

Leu Ala Arg Ile Gly Arg Ile Leu Arg Leu Ile Lys Gly Ala Lys Gly
            165                 170                 175

Ile Arg Thr Leu Leu Phe Ala Leu Met Met Ser Leu Pro Ala Leu Phe
            180                 185                 190

Asn Ile Gly Leu Leu Leu Phe Leu Val Met Phe Ile Tyr Ala Ile Phe
            195                 200                 205

Gly Met Ser Asn Phe Ala Tyr Val Lys Lys Glu Ala Gly Ile Asp Asp
210                 215                 220

Met Phe Asn Phe Glu Thr Phe Gly Asn Gly Met Ile Cys Leu Phe Gln
225                 230                 235                 240

Ile Thr Thr Ser Ala Gly Trp Gly Gly Leu Leu Ala Pro Ile Leu Asn
            245                 250                 255

Ser Ala Pro Pro Asp Cys Asp Pro Asp Thr Ile His Pro Gly Ser Ser
            260                 265                 270

Val Lys Gly Asp Cys Gly Asn Pro Ser Val Gly Ile Phe Phe Phe Val
            275                 280                 285

Ser Tyr Ile Ile Ile Ser Phe Leu Val Val Val Asn Met Tyr Ile Ala
            290                 295                 300

Val Ile Leu Glu Asn
305

(2) INFORMATION FOR SEQ ID NO:5:

(i) SEQUENCE CHARACTERISTICS:
        (A) LENGTH: 309 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:5:

Gly Val Ile Met Asp Asn Phe Asn Gln Gln Lys Lys Phe Gly Gly
  1               5                  10                  15

Gln Asp Ile Phe Met Thr Glu Glu Gln Lys Lys Tyr Tyr Asn Ala Met
            20                  25                  30

Lys Lys Leu Gly Ser Lys Lys Pro Gln Lys Pro Ile Pro Arg Pro Ala
            35                  40                  45
```

-continued

```
Asn Lys Phe Gln Gly Met Val Phe Asp Phe Val Thr Lys Gln Val Phe
 50                  55                  60

Asp Ile Ser Ile Met Ile Leu Ile Cys Leu Asn Met Val Thr Met Met
 65                  70                  75                  80

Val Glu Thr Asp Asp Gln Ser Gln Glu Met Thr Asn Ile Leu Tyr Trp
                 85                  90                  95

Ile Asn Leu Val Phe Ile Val Leu Phe Thr Gly Glu Phe Val Leu Lys
                100                 105                 110

Leu Val Ser Leu Arg His Tyr Tyr Phe Thr Ile Gly Trp Asn Ile Phe
                115                 120                 125

Asp Phe Val Val Val Ile Leu Ser Ile Val Gly Met Phe Leu Ala Glu
                130                 135                 140

Met Ile Glu Lys Tyr Phe Val Ser Pro Thr Leu Phe Arg Val Ile Arg
145                 150                 155                 160

Leu Ala Arg Ile Gly Arg Ile Leu Arg Leu Ile Lys Gly Ala Lys Gly
                165                 170                 175

Ile Arg Thr Leu Leu Phe Ala Leu Met Met Ser Leu Pro Ala Leu Phe
                180                 185                 190

Asn Ile Gly Leu Leu Leu Phe Leu Val Met Phe Ile Tyr Ala Ile Phe
                195                 200                 205

Gly Met Ser Asn Phe Ala Tyr Val Lys Lys Glu Ala Gly Ile Asp Asp
                210                 215                 220

Met Phe Asn Phe Glu Ser Phe Gly Asn Ser Met Ile Cys Leu Phe Gln
225                 230                 235                 240

Ile Thr Thr Ser Ala Gly Trp Asp Gly Leu Leu Ala Pro Ile Leu Asn
                245                 250                 255

Ser Ala Pro Pro Asp Cys Asp Pro Asp Thr Ile His Pro Gly Ser Ser
                260                 265                 270

Val Lys Gly Asp Cys Gly Asn Pro Ser Val Gly Ile Phe Phe Phe Val
                275                 280                 285

Ser Tyr Ile Ile Ile Ser Phe Leu Val Val Val Asn Met Tyr Ile Ala
                290                 295                 300

Val Ile Leu Glu Asn
305

(2) INFORMATION FOR SEQ ID NO:6:

(i) SEQUENCE CHARACTERISTICS:
        (A) LENGTH: 309 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:6:

Gly Val Ile Met Asp Asn Phe Asn Gln Gln Lys Lys Phe Gly Gly
 1                   5                  10                  15

Gln Asp Ile Phe Met Thr Glu Glu Gln Lys Lys Tyr Tyr Asn Ala Met
                 20                  25                  30

Lys Lys Leu Gly Ser Lys Lys Pro Gln Lys Pro Ile Pro Arg Pro Ala
                 35                  40                  45

Asn Lys Phe Gln Gly Met Val Phe Asp Phe Val Thr Arg Gln Val Phe
 50                  55                  60

Asp Ile Ser Ile Val Ile Leu Ile Cys Leu Asn Met Val Thr Met Met
 65                  70                  75                  80
```

-continued

```
Val Glu Thr Asp Asp Gln Gly Lys Tyr Met Thr Leu Val Leu Ser Arg
             85                  90                  95
Ile Asn Leu Val Phe Ile Val Leu Phe Thr Gly Glu Phe Val Leu Lys
            100                 105                 110
Leu Val Ser Leu Arg His Tyr Tyr Phe Thr Ile Gly Trp Asn Ile Phe
            115                 120                 125
Asp Phe Val Val Val Ile Leu Ser Ile Val Gly Met Phe Leu Ala Glu
            130                 135                 140
Met Ile Glu Lys Tyr Phe Val Ser Pro Thr Leu Phe Arg Val Ile Arg
145                 150                 155                 160
Leu Ala Arg Ile Gly Arg Ile Leu Arg Leu Ile Lys Gly Glu Arg Gly
                165                 170                 175
Ser Arg Thr Leu Leu Phe Ala Leu Met Met Ser Leu Pro Ala Leu Phe
            180                 185                 190
Asn Ile Gly Leu Leu Leu Phe Leu Val Met Phe Ile Tyr Ala Ile Phe
            195                 200                 205
Gly Met Ser Asn Phe Ala Tyr Val Lys Lys Glu Ala Gly Ile Asp Asp
            210                 215                 220
Met Phe Asn Phe Glu Thr Phe Gly Asn Ser Met Ile Cys Leu Phe Gln
225                 230                 235                 240
Ile Thr Thr Ser Ala Gly Trp Asp Gly Leu Leu Ala Pro Ile Leu Asn
                245                 250                 255
Ser Ala Pro Pro Asp Cys Asp Pro Asp Thr Ile His Pro Gly Ser Ser
            260                 265                 270
Val Lys Gly Asp Cys Gly Asn Pro Ser Val Gly Ile Phe Phe Phe Val
            275                 280                 285
Ser Tyr Ile Ile Ile Ser Ser Leu Val Val Val Asn Met Tyr Ile Ala
            290                 295                 300
Val Ile Leu Glu Asn
305
```

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

GGGCGGCCGC GGNTGGWTNV AWRTHATG                                      28

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

GTTYTCNARR ATNACNGCRA TRTAC                                          25

(2) INFORMATION FOR SEQ ID NO:9:

(i) SEQUENCE CHARACTERISTICS:

-continued

```
          (A) LENGTH: 30 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:9:

GGGCGGCCGC GTNATHATNG AYAAYTTYAA                                        30

(2) INFORMATION FOR SEQ ID NO:10:

(i) SEQUENCE CHARACTERISTICS:
          (A) LENGTH: 310 amino acids
          (B) TYPE: amino acid
          (C) STRANDEDNESS: Not Relevant
          (D) TOPOLOGY: linear (ii) MOLECULE TYPE: protein (xi) SEQUENCE DESCRIPTION: SEQ ID NO:10:
```

| | | | | | | | | | | | | | | |
|---|---|---|---|---|---|---|---|---|---|---|---|---|---|---|
|Gly|Val|Ile|Ile|Asp|Asn|Phe|Asn|Gln|Gln|Lys|Lys|Phe|Gly|Gly|
|1| | | |5| | | | |10| | | | |15|

Gln Asp Ile Phe Met Thr Glu Glu Gln Lys Lys Tyr Tyr Asn Ala Met
                20                  25                  30

Lys Lys Leu Gly Ser Lys Pro Gln Lys Pro Ile Pro Arg Pro Ala
            35                  40                  45

Asn Lys Phe Gln Gly Met Val Phe Asp Phe Val Thr Lys Gln Val Phe
50                  55                  60

Asp Ile Ser Ile Met Ile Leu Ile Cys Leu Asn Met Val Thr Met Met
65                  70                  75                  80

Val Glu Thr Asp Asp Gln Ser Gln Glu Met Thr Asn Ile Leu Tyr Trp
                85                  90                  95

Ile Asn Leu Val Phe Ile Val Leu Phe Thr Gly Glu Cys Val Leu Lys
            100                 105                 110

Leu Ile Ser Leu Arg Tyr Tyr Tyr Phe Thr Ile Gly Trp Asn Ile Phe
            115                 120                 125

Asp Phe Val Val Val Ile Leu Ser Ile Val Gly Met Phe Leu Ala Glu
            130                 135                 140

Leu Ile Glu Lys Tyr Phe Val Ser Pro Thr Leu Phe Arg Val Ile Arg
145                 150                 155                 160

Leu Ala Arg Ile Gly Arg Ile Leu Arg Leu Ile Lys Gly Ala Lys Gly
                165                 170                 175

Ile Arg Thr Leu Leu Phe Ala Leu Met Met Ser Leu Pro Ala Leu Phe
            180                 185                 190

Asn Ile Gly Leu Leu Leu Phe Leu Val Met Phe Ile Tyr Ala Ile Phe
            195                 200                 205

Gly Met Ser Asn Phe Ala Tyr Val Lys Arg Glu Val Gly Ile Asp Asp
            210                 215                 220

Met Phe Asn Phe Glu Thr Phe Gly Asn Ser Met Ile Cys Leu Phe Gln
225                 230                 235                 240

Ile Thr Thr Ser Ala Gly Trp Asp Gly Leu Leu Ala Pro Ile Leu Asn
                245                 250                 255

Ser Gly Pro Pro Asp Cys Asp Pro Asp Lys Asp His Pro Gly Ser Ser
            260                 265                 270

Val Lys Arg Asp Cys Gly Asn Pro Ser Val Gly Ile Phe Phe Phe Val
            275                 280                 285

Ser Tyr Ile Ile Ile Ser Phe Leu Val Val Leu Asn Met Tyr Ile Ala

```
                    290                 295                 300

Val Ile Leu Glu Asn Phe
305                 310

(2) INFORMATION FOR SEQ ID NO:11:

(i) SEQUENCE CHARACTERISTICS:
        (A) LENGTH: 309 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:11:

Gly Val Ile Ile Asp Asn Phe Asn Gln Gln Lys Lys Lys Leu Gly Gly
1               5                   10                  15

Gln Asp Ile Phe Met Thr Glu Glu Gln Lys Lys Tyr Tyr Asn Ala Met
                20                  25                  30

Lys Lys Leu Gly Ser Lys Lys Pro Gln Lys Pro Ile Pro Arg Pro Leu
            35                  40                  45

Asn Lys Tyr Gln Gly Phe Ile Phe Asp Ile Val Thr Lys Gln Ala Phe
50                  55                  60

Asp Val Thr Ile Met Phe Leu Ile Cys Leu Asn Met Val Thr Met Met
65                  70                  75                  80

Val Glu Thr Asp Asp Gln Ser Pro Glu Lys Ile Asn Ile Leu Ala Lys
                85                  90                  95

Ile Asn Leu Leu Phe Val Ala Ile Phe Thr Gly Glu Cys Ile Val Lys
            100                 105                 110

Leu Ala Ala Leu Arg His Tyr Tyr Phe Thr Asn Ser Trp Asn Ile Phe
        115                 120                 125

Asp Phe Val Val Ile Leu Ser Ile Val Gly Thr Val Leu Ser Asp
    130                 135                 140

Ile Ile Gln Lys Tyr Phe Val Ser Pro Thr Leu Phe Arg Val Ile Arg
145                 150                 155                 160

Leu Ala Arg Ile Gly Arg Ile Leu Arg Leu Ile Arg Gly Ala Lys Gly
                165                 170                 175

Ile Arg Thr Leu Leu Phe Ala Leu Met Met Ser Leu Pro Ala Leu Phe
            180                 185                 190

Asn Ile Gly Leu Leu Leu Phe Leu Val Met Phe Ile Tyr Ser Ile Phe
        195                 200                 205

Gly Met Ala Asn Phe Ala Tyr Val Lys Trp Glu Ala Gly Ile Asp Asp
    210                 215                 220

Met Phe Asn Phe Gln Thr Phe Ala Asn Ser Met Leu Cys Leu Phe Gln
225                 230                 235                 240

Ile Thr Thr Ser Ala Gly Trp Asp Gly Leu Leu Ser Pro Ile Leu Asn
                245                 250                 255

Thr Gly Pro Pro Tyr Cys Asp Pro Thr Leu Pro Asn Ser Asn Gly Ser
            260                 265                 270

Arg Gly Asp Cys Gly Ser Pro Ala Val Gly Ile Leu Phe Phe Thr Thr
        275                 280                 285

Tyr Ile Ile Ile Ser Phe Leu Ile Val Val Asn Met Tyr Ile Ala Ile
    290                 295                 300

Ile Leu Glu Asn Phe
305
```

(2) INFORMATION FOR SEQ ID NO:12:

(i) SEQUENCE CHARACTERISTICS:
        (A) LENGTH: 310 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:12:

```
Gly Val Ile Ile Asp Asn Phe Asn Gln Gln Lys Lys Lys Leu Gly Gly
1               5                   10                  15

Lys Asp Ile Phe Met Thr Glu Glu Gln Lys Lys Tyr Tyr Asn Ala Met
                20                  25                  30

Lys Lys Leu Gly Ser Lys Lys Pro Gln Lys Pro Ile Pro Arg Pro Gln
            35                  40                  45

Asn Lys Ile Gln Gly Met Val Tyr Asp Leu Val Thr Lys Gln Ala Phe
        50                  55                  60

Asp Ile Thr Ile Met Ile Leu Ile Cys Leu Asn Met Val Thr Met Met
65                  70                  75                  80

Val Glu Thr Asp Asp Gln Ser Gln Leu Lys Val Asp Ile Leu Tyr Asn
                85                  90                  95

Ile Asn Met Ile Phe Ile Ile Phe Thr Gly Glu Cys Val Leu Lys
                100                 105                 110

Met Leu Ala Leu Arg Gln Tyr Tyr Phe Thr Val Gly Trp Asn Ile Phe
            115                 120                 125

Asp Phe Val Val Val Ile Leu Ser Ile Val Gly Leu Ala Leu Ser Asp
        130                 135                 140

Leu Ile Gln Lys Tyr Phe Val Ser Pro Thr Leu Phe Arg Val Ile Arg
145                 150                 155                 160

Leu Ala Arg Ile Gly Arg Val Leu Arg Leu Ile Arg Gly Ala Lys Gly
                165                 170                 175

Ile Arg Thr Leu Leu Phe Ala Leu Met Met Ser Leu Pro Ala Leu Phe
                180                 185                 190

Asn Ile Gly Leu Leu Leu Phe Leu Val Met Phe Ile Tyr Ser Ile Phe
            195                 200                 205

Gly Met Ser Asn Phe Ala Tyr Val Lys Lys Glu Ser Gly Ile Asp Asp
        210                 215                 220

Met Phe Asn Phe Glu Thr Phe Gly Asn Ser Ile Ile Cys Leu Phe Glu
225                 230                 235                 240

Ile Thr Thr Ser Ala Gly Trp Asp Gly Leu Leu Asn Pro Ile Leu Asn
                245                 250                 255

Ser Gly Pro Pro Asp Cys Asp Pro Asn Leu Glu Asn Pro Gly Thr Ser
                260                 265                 270

Val Lys Gly Asp Cys Gly Asn Pro Ser Ile Gly Ile Cys Phe Phe Cys
            275                 280                 285

Ser Tyr Ile Ile Ile Ser Phe Leu Ile Val Val Asn Met Tyr Ile Ala
        290                 295                 300

Ile Ile Leu Glu Asn Phe
305                 310
```

(2) INFORMATION FOR SEQ ID NO:13:

(i) SEQUENCE CHARACTERISTICS:
        (A) LENGTH: 310 amino acids
        (B) TYPE: amino acid
        (C) STRANDEDNESS: Not Relevant -continued (D) TOPOLOGY: linear (ii) MOLECULE TYPE: protein (xi) SEQUENCE DESCRIPTION: SEQ ID NO:13:

```
Gly Val Ile Ile Asp Asn Phe Asn Gln Gln Lys Lys Phe Gly Gly
1               5                   10                  15

Gln Asp Ile Phe Met Thr Glu Glu Gln Lys Lys Tyr Tyr Asn Ala Met
            20                  25                  30

Lys Lys Leu Gly Ser Lys Lys Pro Gln Lys Pro Ile Pro Arg Pro Gly
                35                  40                  45

Asn Lys Phe Gln Gly Met Val Phe Asp Phe Val Thr Arg Gln Val Phe
        50                  55                  60

Asp Ile Ser Ile Met Ile Leu Ile Cys Leu Asn Met Val Thr Met Met
65                  70                  75                  80

Val Glu Thr Asp Asp Gln Ser Asp Tyr Val Thr Ser Ile Leu Ser Arg
                85                  90                  95

Ile Asn Leu Val Phe Ile Val Leu Phe Thr Gly Glu Cys Val Leu Lys
                100                 105                 110

Leu Ile Ser Leu Arg His Tyr Tyr Phe Thr Ile Gly Trp Asn Ile Phe
            115                 120                 125

Asp Phe Val Val Val Ile Leu Ser Ile Val Gly Met Phe Leu Ala Glu
        130                 135                 140

Leu Ile Glu Lys Tyr Phe Val Ser Pro Thr Leu Phe Arg Val Ile Arg
145                 150                 155                 160

Leu Ala Arg Ile Gly Arg Ile Leu Arg Leu Ile Lys Gly Ala Lys Gly
                165                 170                 175

Ile Arg Thr Leu Leu Phe Ala Leu Met Met Ser Leu Pro Ala Leu Phe
            180                 185                 190

Asn Ile Gly Leu Leu Leu Phe Leu Val Met Phe Ile Tyr Ala Ile Phe
        195                 200                 205

Gly Met Ser Asn Phe Ala Tyr Val Lys Arg Glu Val Gly Ile Asp Asp
        210                 215                 220

Met Phe Asn Phe Glu Thr Phe Gly Asn Ser Met Ile Cys Leu Phe Gln
225                 230                 235                 240

Ile Thr Thr Ser Ala Gly Trp Asp Gly Leu Leu Ala Pro Ile Leu Asn
                245                 250                 255

Ser Lys Pro Pro Asp Cys Asp Pro Asn Lys Val Asn Pro Gly Ser Ser
            260                 265                 270

Val Lys Gly Asp Cys Gly Asn Pro Ser Val Gly Ile Phe Phe Phe Val
        275                 280                 285

Ser Tyr Ile Ile Ile Ser Phe Leu Val Val Val Asn Met Tyr Ile Ala
        290                 295                 300

Val Ile Leu Glu Asn Phe
305                 310
```

(2) INFORMATION FOR SEQ ID NO:14:

(i) SEQUENCE CHARACTERISTICS:
(A) LENGTH: 310 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:14:

```
Gly Val Ile Ile Asp Asn Phe Asn Gln Gln Lys Lys Phe Gly Gly
1               5                   10                  15

Gln Asp Ile Phe Met Thr Glu Glu Gln Lys Lys Tyr Tyr Asn Ala Met
                20                  25                  30

Lys Lys Leu Gly Ser Lys Lys Pro Gln Lys Pro Ile Pro Arg Pro Ala
            35                  40                  45

Asn Lys Phe Gln Gly Met Val Phe Asp Phe Val Thr Lys Gln Val Phe
    50                  55                      60

Asp Ile Ser Ile Met Ile Leu Ile Cys Leu Asn Met Val Thr Met Met
65                  70                  75                  80

Val Glu Thr Asp Asp Gln Ser Gln Glu Met Thr Asn Ile Leu Tyr Trp
                85                  90                  95

Ile Asn Leu Val Phe Ile Val Leu Phe Thr Gly Glu Cys Val Leu Lys
            100                 105                 110

Leu Ile Ser Leu Arg His Tyr Tyr Phe Thr Ile Gly Trp Asn Ile Phe
        115                 120                 125

Asp Phe Val Val Ile Leu Ser Ile Val Gly Met Phe Leu Ala Glu
        130                 135                 140

Leu Ile Glu Lys Tyr Phe Val Ser Pro Thr Leu Phe Arg Val Ile Arg
145                 150                 155                 160

Leu Ala Arg Ile Gly Arg Ile Leu Arg Leu Ile Lys Gly Ala Lys Gly
                165                 170                 175

Ile Arg Thr Leu Leu Phe Ala Leu Met Met Ser Leu Pro Ala Leu Phe
            180                 185                 190

Asn Ile Gly Leu Leu Leu Phe Leu Val Met Phe Ile Tyr Ala Ile Phe
        195                 200                 205

Gly Met Ser Asn Phe Ala Tyr Val Lys Arg Glu Val Gly Ile Asp Asp
    210                 215                 220

Met Phe Asn Phe Glu Thr Phe Gly Asn Ser Met Ile Cys Leu Phe Gln
225                 230                 235                 240

Ile Thr Thr Ser Ala Gly Trp Asp Gly Leu Leu Ala Pro Ile Leu Asn
            245                 250                 255

Ser Gly Pro Pro Asp Cys Asp Pro Glu Lys Asp His Pro Gly Ser Ser
            260                 265                 270

Val Lys Gly Asp Cys Gly Asn Pro Ser Val Gly Ile Phe Phe Phe Val
        275                 280                 285

Ser Tyr Ile Ile Ile Ser Phe Leu Val Val Val Asn Met Tyr Ile Ala
    290                 295                 300

Val Ile Leu Glu Asn Phe
305                 310

(2) INFORMATION FOR SEQ ID NO:15:

(i) SEQUENCE CHARACTERISTICS:
        (A) LENGTH: 310 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:15:

Gly Val Ile Ile Asp Asn Phe Asn Gln Gln Lys Lys Phe Gly Gly
1               5                   10                  15

Gln Asp Ile Phe Met Thr Glu Glu Gln Lys Lys Tyr Tyr Asn Ala Met
                20                  25                  30
```

```
Lys Lys Leu Gly Ser Lys Lys Pro Gln Lys Pro Ile Pro Arg Pro Ala
            35                  40                  45

Asn Lys Phe Gln Gly Met Val Phe Asp Phe Val Thr Arg Gln Val Phe
        50                  55                  60

Asp Ile Ser Ile Met Ile Leu Ile Cys Leu Asn Met Val Thr Met Met
65                      70                  75                  80

Val Glu Thr Asp Asp Gln Ser Lys Tyr Met Thr Leu Val Leu Ser Arg
                    85                  90                  95

Ile Asn Leu Val Phe Ile Val Leu Phe Thr Gly Glu Phe Leu Leu Lys
                100                 105                 110

Leu Ile Ser Leu Arg Tyr Tyr Tyr Phe Thr Ile Gly Trp Asn Ile Phe
        115                 120                 125

Asp Phe Val Val Ile Leu Ser Ile Val Gly Met Phe Leu Ala Glu
        130                 135             140

Leu Ile Glu Lys Tyr Phe Val Ser Pro Thr Leu Phe Arg Val Ile Arg
145                 150                 155                 160

Leu Ala Arg Ile Gly Arg Ile Leu Arg Leu Ile Lys Gly Ala Lys Gly
                165                 170                 175

Ile Arg Thr Leu Leu Phe Ala Leu Met Met Ser Leu Pro Ala Leu Phe
                180                 185                 190

Asn Ile Gly Leu Leu Leu Phe Leu Val Met Phe Ile Tyr Ala Ile Phe
            195                 200                 205

Gly Met Ser Asn Phe Ala Tyr Val Lys Lys Glu Ala Gly Ile Asp Asp
    210                 215                 220

Met Phe Asn Phe Glu Thr Phe Gly Asn Ser Met Ile Cys Leu Phe Gln
225                 230                 235                 240

Ile Thr Thr Ser Ala Gly Trp Asp Gly Leu Leu Ala Pro Ile Leu Asn
                245                 250                 255

Ser Ala Pro Pro Asp Cys Asp Pro Asp Ala Ile His Pro Gly Ser Ser
                260                 265                 270

Val Lys Gly Asp Cys Gly Asn Pro Ser Val Gly Ile Phe Phe Phe Val
            275                 280                 285

Ser Tyr Ile Ile Ile Ser Phe Leu Val Val Val Asn Met Tyr Ile Ala
        290                 295                 300

Val Ile Leu Glu Asn Phe
305             310

(2) INFORMATION FOR SEQ ID NO:16:

(i) SEQUENCE CHARACTERISTICS:
        (A) LENGTH: 310 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:16:

Gly Val Ile Ile Asp Asn Phe Asn Arg Gln Lys Gln Lys Leu Gly Gly
1               5                   10                  15

Glu Asp Leu Phe Met Thr Glu Glu Gln Lys Lys Tyr Tyr Asn Ala Met
            20                  25                  30

Lys Lys Leu Gly Ser Lys Lys Ala Ala Lys Cys Ile Pro Arg Pro Ser
            35                  40                  45

Asn Val Val Gln Gly Val Val Tyr Asp Ile Val Thr Gln Pro Phe Thr
        50                  55                  60
```

-continued

```
Asp Ile Phe Ile Met Ala Leu Ile Cys Ile Asn Met Val Ala Met Met
 65                  70                  75                  80

Val Glu Ser Glu Asp Gln Ser Gln Val Lys Lys Asp Ile Leu Ser Gln
                 85                  90                  95

Ile Asn Val Ile Phe Val Ile Phe Thr Val Glu Cys Leu Leu Lys
            100                 105                 110

Leu Leu Ala Leu Arg Gln Tyr Phe Phe Thr Val Gly Trp Asn Val Phe
            115                 120                 125

Asp Phe Ala Val Val Ile Ser Ile Gly Leu Leu Leu Ser Asp
130                 135                 140

Ile Ile Glu Lys Tyr Phe Val Ser Pro Thr Leu Phe Arg Val Ile Arg
145                 150                 155                 160

Leu Ala Arg Ile Ala Arg Val Leu Arg Leu Ile Arg Ala Ala Lys Gly
                165                 170                 175

Ile Arg Thr Leu Leu Phe Ala Leu Met Met Ser Leu Pro Ala Leu Phe
            180                 185                 190

Asn Ile Gly Leu Leu Leu Phe Leu Ile Met Phe Ile Phe Ser Ile Phe
            195                 200                 205

Gly Met Ser Asn Phe Ala Tyr Val Lys Lys Gln Gly Gly Val Asp Asp
210                 215                 220

Ile Phe Asn Phe Glu Thr Phe Gly Asn Ser Met Ile Cys Leu Phe Glu
225                 230                 235                 240

Ile Thr Thr Ser Ala Gly Trp Asp Gly Leu Leu Pro Thr Leu Asn
            245                 250                 255

Thr Gly Pro Pro Asp Cys Asp Pro Asp Val Glu Asn Pro Gly Thr Asp
                260                 265                 270

Val Arg Gly Asn Cys Gly Asn Pro Gly Lys Gly Ile Thr Phe Phe Cys
            275                 280                 285

Ser Tyr Ile Ile Leu Ser Phe Leu Val Val Val Asn Met Tyr Ile Ala
            290                 295                 300

Val Ile Leu Glu Asn Phe
305                 310

(2) INFORMATION FOR SEQ ID NO:17:

(i) SEQUENCE CHARACTERISTICS:
        (A) LENGTH: 317 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:17:

Gly Val Ile Ile Asp Lys Phe Ser Phe Leu Lys Lys Tyr Asp Gly
 1               5                  10                  15

Thr Tyr Leu Asp Met Phe Leu Thr Pro Thr Gln Gln Asn Tyr Tyr Asn
                20                  25                  30

Thr Leu Lys Lys Leu Gly Thr Lys Pro Gln Lys Thr Val Lys Arg
            35                  40                  45

Pro Lys Asn Lys Cys Gln Ala Val Val Tyr Asp Leu Val Met Ser Asn
 50                 55                  60

Gln Phe Glu Ile Phe Ile Thr Ile Ile Thr Asn Met Ile Phe
 65                 70                  75                  80

Met Ala Phe Glu His Tyr Asn Gln Ser Glu Val Val Thr Glu Val Leu
                85                  90                  95
```

```
Ala Thr Ala Asn Ile Ala Phe Thr Ile Leu Tyr Ala Val Glu Ala Ile
                100                 105                 110

Ile Lys Ile Ile Gly Leu Arg Ile His Tyr Leu Arg Asn Leu Trp Asn
        115                 120                 125

Val Phe Asp Phe Leu Val Val Thr Leu Ser Val Met Asp Ala Phe Leu
    130                 135                 140

Asn Asp Ile Phe Gly Asp Gly Ile Phe Met Asn Pro Ser Leu Leu Arg
145                 150                 155                 160

Val Ala Arg Met Phe Arg Ile Gly Arg Ile Ile Arg Leu Ile Lys Trp
                165                 170                 175

Ala Lys Gly Met Arg Lys Leu Leu Phe Ala Leu Val Ile Ser Leu Pro
            180                 185                 190

Ala Leu Phe Asn Ile Gly Ala Leu Leu Met Leu Val Met Phe Ile Tyr
        195                 200                 205

Thr Ile Ile Gly Met Ser Ser Phe Gly Gln Ile Lys Leu Ser Gly Ala
    210                 215                 220

Leu Asn Asp Gln Val Asn Phe Gln Thr Phe Gly Lys Thr Phe Leu Leu
225                 230                 235                 240

Leu Val Arg Leu Ala Thr Ser Ala Gly Trp Asn Asp Ile Leu Gly Pro
                245                 250                 255

Leu Leu Ile Gln Pro Pro Asn Cys Asp Pro Asn Tyr Ile Thr Thr Ser
            260                 265                 270

Thr Gly Glu Lys Ile Lys Val Val Asn Gly Asp Cys Gly Met Pro Trp
        275                 280                 285

Leu Ala Ile Ser Tyr Met Val Ser Tyr Ile Ile Ile Val Phe Met Ile
    290                 295                 300

Val Phe Asn Met Tyr Ile Ala Val Ile Leu Glu Asn Phe
305                 310                 315

(2) INFORMATION FOR SEQ ID NO:18:

(i) SEQUENCE CHARACTERISTICS:
        (A) LENGTH: 311 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:18:

Gly Val Ile Ile Asp Asn Phe Asn Gln Gln Lys Lys Gly Ala Gly Gly
1               5                   10                  15

Ser Leu Glu Val Phe Met Thr Asp Gln Lys Lys Tyr Tyr Lys Ala
            20                  25                  30

Met Lys Asn Leu Gln Ser Lys Lys Pro Thr Lys Gly Ile Pro Met Pro
        35                  40                  45

Gly Phe Lys Ile Ala Glu Trp Met Phe His Leu Thr Thr Asn Gln Lys
    50                  55                  60

Phe Asp Val Ala Ile Met Met Val Ile Leu Leu Asn Met Ile Thr Met
65                  70                  75                  80

Ala Met Glu His Tyr Asn Met Ser Arg Thr Phe Glu Asp Phe Leu Lys
                85                  90                  95

Tyr Ile Asn Met Val Phe Ile Gly Ile Phe Thr Gly Glu Cys Val Met
            100                 105                 110

Lys Leu Met Gly Leu Arg Phe Tyr Phe Lys Glu Pro Trp Asn Ile
        115                 120                 125
```

```
Phe Asp Phe Val Val Val Leu Ser Ile Leu Gly Ile Ala Leu Ser
    130                 135                 140

Asp Ile Ile Lys Gln Tyr Phe Val Ser Pro Thr Leu Leu Arg Val Val
145                 150                 155                 160

Arg Val Phe Arg Val Gly Arg Val Leu Arg Leu Val Lys Ser Ala Lys
                165                 170                 175

Gly Ile Arg Thr Leu Leu Phe Ser Leu Ala Val Ser Leu Pro Ala Leu
            180                 185                 190

Phe Asn Ile Gly Leu Leu Leu Phe Leu Val Met Phe Ile Tyr Ser Met
        195                 200                 205

Phe Gly Met Ser Phe Phe Met Asp Val Gly Tyr Phe Asp Gly Ile Asp
    210                 215                 220

Asp Val Phe Asn Phe Gln Thr Leu Ile Gln Ser Met Ile Leu Leu Phe
225                 230                 235                 240

Gln Met Ser Thr Ser Ala Gly Trp Asp Gly Val Leu Ala Ala Ile Met
                245                 250                 255

Arg Glu Pro Pro Ala Cys Gln Pro Asp Leu Lys Ile Phe Gly Ser Lys
                260                 265                 270

Ser Asn Asn Gly Asn Cys Gly Asn Tyr Gly Met Ala Val Met Phe Leu
            275                 280                 285

Val Thr Tyr Leu Val Ile Ser Phe Leu Val Val Ile Asn Met Tyr Ile
        290                 295                 300

Ala Val Ile Leu Glu Asn Phe
305                 310

(2) INFORMATION FOR SEQ ID NO:19:

(i) SEQUENCE CHARACTERISTICS:
        (A) LENGTH: 307 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:19:

Gly Val Ile Ile Asp Asn Phe Asn Glu Gln Lys Lys Lys Ala Gly Gly
1               5                   10                  15

Ser Leu Glu Met Phe Met Thr Glu Asp Gln Lys Lys Tyr Tyr Ser Ala
                20                  25                  30

Met Lys Lys Met Gly Ser Lys Lys Pro Leu Lys Ala Ile Pro Arg Pro
            35                  40                  45

Arg Trp Arg Pro Gln Ala Ile Val Phe Glu Ile Val Thr Asp Lys Lys
        50                  55                  60

Phe Asp Ile Ile Ile Met Leu Phe Ile Gly Leu Asn Met Phe Thr Met
65                  70                  75                  80

Thr Leu Asp Arg Tyr Asp Ala Ser Asp Thr Tyr Asn Ala Val Leu Asp
                85                  90                  95

Tyr Leu Asn Ala Ile Phe Val Val Ile Phe Ser Ser Glu Cys Leu Leu
            100                 105                 110

Lys Ile Phe Ala Leu Arg Tyr His Tyr Phe Ile Glu Pro Trp Asn Leu
        115                 120                 125

Phe Asp Val Val Val Val Ile Leu Ser Ile Leu Gly Leu Val Leu Ser
    130                 135                 140

Asp Ile Ile Glu Lys Tyr Phe Val Ser Pro Thr Leu Leu Arg Val Val
145                 150                 155                 160
```

-continued

```
Arg Val Ala Lys Val Gly Arg Val Leu Arg Leu Val Lys Gly Ala Lys
                165                 170                 175
Gly Ile Arg Thr Leu Leu Phe Ala Leu Ala Met Ser Leu Pro Ala Leu
            180                 185                 190
Phe Asn Ile Cys Leu Leu Leu Phe Leu Val Met Phe Ile Phe Ala Ile
        195                 200                 205
Phe Gly Met Ser Phe Phe Met His Val Lys Glu Lys Ser Gly Ile Asn
    210                 215                 220
Asp Val Tyr Asn Phe Lys Thr Phe Gly Gln Ser Met Ile Leu Leu Phe
225                 230                 235                 240
Gln Met Ser Thr Ser Ala Gly Trp Asp Gly Val Leu Asp Ala Ile Ile
                245                 250                 255
Asn Glu Glu Ala Cys Asp Pro Asp Asn Asp Lys Gly Tyr Pro Gly
            260                 265                 270
Asn Cys Gly Ser Ala Thr Val Gly Ile Thr Phe Leu Leu Ser Tyr Leu
        275                 280                 285
Val Ile Ser Phe Leu Ile Val Ile Asn Met Tyr Ile Ala Val Ile Leu
    290                 295                 300
Glu Asn Gly
305
```

(2) INFORMATION FOR SEQ ID NO:20:

(i) SEQUENCE CHARACTERISTICS:
        (A) LENGTH: 312 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:20:

```
Gly Val Ile Ile Asp Asn Phe Asn Arg Leu Lys Gln Gln Tyr Glu Asp
1               5                   10                  15
Gly Val Gly Ile Phe Leu Thr Pro Gly Gln Arg Asn Trp Val Asn Thr
            20                  25                  30
Leu Lys Ser Ala Ala Gly Lys Lys Pro Thr Arg Arg Leu Thr Arg Pro
        35                  40                  45
Lys Ser Lys Trp Arg Ala Thr Leu Phe Asp Phe Ile Gly Lys Lys Gln
    50                  55                  60
Phe Glu Leu Phe Ile Met Ser Val Ile Ala Asn Met Leu Thr Met
65                  70                  75                  80
Met Ile Gln His Tyr Asp Gln Thr Lys Glu Val Glu Val Ala Leu Asn
                85                  90                  95
Tyr Leu Asn Tyr Leu Phe Thr Gly Ile Phe Thr Ile Glu Ala Ile Ile
            100                 105                 110
Arg Leu Val Ala Met Ala Leu Glu Tyr Phe Lys Ser Phe Met Asn Ile
        115                 120                 125
Phe Asp Phe Thr Ile Val Leu Ile Ser Ile Ala Val Ile Val Tyr Glu
    130                 135                 140
Ser Ser Lys Ser Ser Thr Asp Asn Leu Asn Phe Ser Pro Gly Leu Leu
145                 150                 155                 160
Arg Val Ile Arg Val Phe Arg Leu Gly Arg Leu Leu Arg Phe Phe Asp
                165                 170                 175
Gly Ala Lys Gly Ile Arg Gln Leu Leu Phe Thr Ile Val Lys Ser Ala
            180                 185                 190
```

```
Pro Ala Leu Leu Asn Ile Gly Thr Leu Leu Phe Leu Val Met Phe Ile
            195                 200                 205

Tyr Ala Val Met Gly Met Asn Phe Phe Met Tyr Val Ala Glu Thr Gly
            210                 215                 220

Ala Phe Asn Gln Val Val Asn Phe Lys Thr Phe Gly Ser Ser Met Cys
225                 230                 235                 240

Leu Leu Phe Arg Ile Ser Thr Ala Ala Gly Trp Asn Gly Val Leu Glu
                245                 250                 255

Ala Ala Met Val Gln Pro Pro Lys Cys Ser Lys Leu Lys Thr Ala Glu
            260                 265                 270

Leu Asn Asn Asn Ser Asn Cys Gly Ser Pro Ile Leu Ala Ile Ile Tyr
                275                 280                 285

Phe Val Ser Tyr Ile Ala Leu Ile Val Leu Ile Met Ile Asn Met Tyr
290                 295                 300

Ile Ala Val Ile Leu Glu Asn Phe
305                 310
```

(2) INFORMATION FOR SEQ ID NO:21:

(i) SEQUENCE CHARACTERISTICS:
        (A) LENGTH: 930 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

```
GGCGTCATNA TNGATAATTT TAACCAGCAG AAAAAGAAGT TTGGAGGTCA AGACATCTTT      60
ATGACAGAGG AACAGAAAAA ATATTACAAT GCAATGAAGA AACTTGGATC CAAGAAACCT     120
CAGAAACCCA TACCTCGCCC AGCAAACAAA TTCCAAGGAA TGGTCTTTGA TTTTGTAACC     180
AGACAAGTCT TTGATATCAG CATCATGATC CTCATCTGCC TCAACATGGT CACCATGATG     240
GTGGAAACGG ATGACCAGGG CAAATACATG ACCCTAGTTT TGTCCCGGAT CAACCTAGTG     300
TTCATTGTTC TGTTCACTGG AGAATTTGTG CTGAAGCTCG TCTCCCTCAG ACACTACTAC     360
TTCACTATAG GCTGGAACAT CTTTGACTTT GTGGTGGTGA TTCTCTCCAT TGTAGGTATG     420
TTTCTGGCTG AGATGATAGA AAAGTATTTT GTGTCCCCTA CCTTGTTCCG AGTGATCCGT     480
CTTGCCAGGA TTGGCCGAAT CCTACGTCTG ATCAAAGGAG CAAAGGGGAT CCGCACGCTG     540
CTCTTTGCTT TGATGATGTC CCTTCCTGCG TTGTTTAACA TCGGCCTCCT GCTCTTCCTG     600
GTCATGTTTA TCTATGCCAT CTTTGGGATG TCCAACTTTG CCTATGTTAA AAAGGAAGCT     660
GGAATTGATG ACATGTTCAA CTTTGAGACC TTTGGCAACA GCATGATCTG CTTGTTCCAA     720
ATTACAACCT CTGCTGGCTG GGATGGATTG CTAGCACCTA TTCTTAATAG TGCACCACCC     780
GACTGTGACC CTGACACAAT TCACCCTGGC AGCTCAGTTA AGGGAGACTG TGGGAACCCA     840
TCTGTTGGGA TTTTCTTTTT TGTCAGTTAC ATCATCATAT CCTTCCTGGT TGTGGTGAAT     900
ATGTATATTG CCGTCATTCT CGAAAACTTT                                      930
```

(2) INFORMATION FOR SEQ ID NO:22:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:22:

Lys Lys Leu Gly Ser Lys Lys
1               5

(2) INFORMATION FOR SEQ ID NO:23:

(i) SEQUENCE CHARACTERISTICS:
      (A) LENGTH: 311 amino acids
      (B) TYPE: amino acid
      (C) STRANDEDNESS: Not Relevant
      (D) TOPOLOGY: linear (ii) MOLECULE TYPE: protein (xi) SEQUENCE DESCRIPTION: SEQ ID NO:23:

Gly Val Ile Ile Asp Asn Phe Asn Gln Gln Lys Lys Leu Gly Gly
1               5                   10                  15

Gln Asp Ile Phe Met Thr Glu Glu Gln Lys Lys Tyr Tyr Asn Ala Met
                20                  25                  30

Lys Lys Leu Gly Ser Lys Pro Gln Lys Pro Ile Pro Arg Pro Leu
                35                  40                  45

Asn Lys Tyr Gln Gly Phe Val Phe Asp Ile Val Thr Arg Gln Ala Phe
50                      55                  60

Asp Ile Ile Ile Met Val Leu Ile Cys Leu Met Asn Ile Thr Met Met
65                      70                  75                  80

Val Glu Thr Asp Glu Gln Gly Glu Glu Lys Thr Lys Val Leu Gly Arg
                85                  90                  95

Ile Asn Gln Phe Phe Val Ala Val Phe Thr Gly Glu Cys Val Met Lys
                100                 105                 110

Met Phe Ala Leu Arg Gln Tyr Tyr Phe Thr Asn Gly Trp Asn Val Phe
                115                 120                 125

Asp Phe Ile Val Val Ile Leu Ser Ile Gly Ser Leu Leu Phe Ser Ala
                130                 135                 140

Ile Leu Lys Ser Leu Glu Asn Tyr Phe Ser Pro Thr Leu Phe Arg Val
145                 150                 155                 160

Ile Arg Leu Ala Arg Ile Gly Arg Ile Leu Arg Leu Ile Arg Ala Ala
                165                 170                 175

Lys Gly Ile Arg Thr Leu Leu Phe Ala Leu Met Met Ser Leu Pro Ala
                180                 185                 190

Leu Phe Asn Ile Gly Leu Leu Leu Phe Leu Val Met Phe Ile Tyr Ser
                195                 200                 205

Ile Phe Gly Met Ala Ser Phe Ala Asn Val Val Asp Glu Ala Gly Ile
                210                 215                 220

Asp Asp Met Phe Asn Phe Lys Thr Phe Gly Asn Ser Met Leu Cys Leu
225                 230                 235                 240

Phe Gln Ile Thr Thr Ser Ala Gly Trp Asp Gly Leu Leu Ser Pro Ile
                245                 250                 255

Leu Asn Thr Gly Pro Pro Tyr Cys Asp Pro Asn Leu Pro Asn Ser Asn
                260                 265                 270

Gly Ser Arg Gly Asn Cys Gly Ser Pro Ala Val Gly Ile Ile Phe Phe
                275                 280                 285

Thr Thr Tyr Ile Ile Ile Ser Phe Leu Ile Val Val Asn Met Tyr Ile
                290                 295                 300

Ala Val Ile Leu Glu Asn Phe
305                 310